(12) United States Patent
Kang et al.

(10) Patent No.: US 8,921,089 B2
(45) Date of Patent: Dec. 30, 2014

(54) ***BRADYRHIZOBIUM* STRAINS**

(71) Applicant: Novozymes BioAg A/S, Bagsvaerd (DK)

(72) Inventors: Yaowei Kang, Christiansburg, VA (US); Anh Tran, Roanoke, VA (US); Shawn Semones, Salem, VA (US)

(73) Assignee: Novozymes BioAg A/S, Bagsvaerd (DK)

( * ) Notice: Subject to any disclaimer, the term of this patent is extended or adjusted under 35 U.S.C. 154(b) by 0 days.

(21) Appl. No.: 13/716,510

(22) Filed: Dec. 17, 2012

(65) Prior Publication Data

US 2013/0157848 A1    Jun. 20, 2013

Related U.S. Application Data

(60) Provisional application No. 61/576,470, filed on Dec. 16, 2011.

(51) Int. Cl.
*C12N 1/20* (2006.01)
*C12R 1/01* (2006.01)
*A01H 3/00* (2006.01)

(52) U.S. Cl.
CPC ... *C12N 1/20* (2013.01); *C12R 1/01* (2013.01); *A01H 3/00* (2013.01)
USPC ...................................... 435/252.1

(58) Field of Classification Search
None
See application file for complete search history.

(56) References Cited

U.S. PATENT DOCUMENTS

| | | |
|---|---|---|
| 4,536,207 A | 8/1985 | McCandliss |
| 4,812,159 A | 3/1989 | Freepons |
| 4,886,541 A | 12/1989 | Hadwiger |
| 4,940,840 A | 7/1990 | Suslow |
| 4,964,894 A | 10/1990 | Freepons |
| 4,978,381 A | 12/1990 | Hadwiger |
| 5,026,417 A | 6/1991 | Kucey |
| 5,057,141 A | 10/1991 | Rodriguez-Kabana |
| 5,104,437 A | 4/1992 | Hadwiger |
| 5,175,149 A | 12/1992 | Stacey |
| 5,321,011 A | 6/1994 | Stacey |
| 5,374,627 A | 12/1994 | Ito |
| 5,454,464 A | 10/1995 | Yamamoto |
| 5,536,155 A | 7/1996 | Futaki |
| 5,549,718 A | 8/1996 | Lerouge |
| 5,554,445 A | 9/1996 | Struszczyk |
| 5,586,411 A | 12/1996 | Gleddie |
| 5,628,810 A | 5/1997 | Dugast |
| 5,696,098 A | 12/1997 | Muraki |
| 5,702,752 A | 12/1997 | Gugger |
| 5,705,634 A | 1/1998 | Bredehorst |
| 5,720,793 A | 2/1998 | Kato |
| 5,726,123 A | 3/1998 | Heinsohn |
| 5,733,851 A | 3/1998 | Villanueva |
| 5,830,459 A | 11/1998 | Cuero |
| 5,965,545 A | 10/1999 | Ben-Shalom |
| 5,990,291 A | 11/1999 | Waggle |
| 6,060,429 A | 5/2000 | Ben-Shalom |
| 6,146,668 A | 11/2000 | Kelly |
| 6,167,652 B1 | 1/2001 | Heinsohn |
| 6,193,988 B1 | 2/2001 | Stoner |
| 6,197,942 B1 | 3/2001 | Muraki |
| 6,200,929 B1 | 3/2001 | Horibe |
| 6,242,381 B1 | 6/2001 | van der Krieken |
| 6,258,749 B1 | 7/2001 | Nonomura |
| 6,352,727 B1 | 3/2002 | Takahashi |
| 6,407,040 B1 | 6/2002 | Nichols |
| 6,413,910 B1 | 7/2002 | Vasiljevich |
| 6,524,998 B1 | 2/2003 | Kloepper |
| 6,589,942 B1 | 7/2003 | Ben-Shalom |
| 6,606,822 B2 * | 8/2003 | Bonfiglio ...................... 47/57.6 |
| 6,649,566 B2 | 11/2003 | Doostdar |
| 6,849,576 B2 | 2/2005 | Suzuki |
| 6,878,819 B1 | 4/2005 | Natunen |
| 6,933,380 B2 | 8/2005 | Huang |
| 6,979,664 B1 | 12/2005 | Smith |
| 7,250,068 B1 | 7/2007 | Smith |
| 7,262,151 B2 | 8/2007 | Smith |
| 7,576,213 B2 | 8/2009 | Flematti |
| 7,619,076 B2 | 11/2009 | Beau |
| 7,637,980 B2 | 12/2009 | Smith |
| 2005/0187107 A1 * | 8/2005 | Smith et al. .................... 504/100 |
| 2007/0027032 A1 | 2/2007 | Chen |
| 2008/0248953 A1 | 10/2008 | Smith |
| 2010/0087369 A1 | 4/2010 | Cutsem |
| 2010/0099560 A1 | 4/2010 | Hnatowich |
| 2012/0252672 A1 * | 10/2012 | Kang et al. .................... 504/117 |

FOREIGN PATENT DOCUMENTS

| | | |
|---|---|---|
| WO | 00/04778 A1 | 2/2000 |
| WO | 2005/062899 A1 | 7/2005 |
| WO | 2005/063784 A1 | 7/2005 |
| WO | 2008/085958 A1 | 7/2008 |
| WO | 2010/049751 A1 | 5/2010 |

OTHER PUBLICATIONS

Radwan, S.S., Dashti, N., El-Nemr, I., and Khanafer, M., "Hydrocarbon utilization by nodule bacteria and plant growth-promoting rhizobacteria", International Journal of Phytoremediation 2007, vol. 9, pp. 475-486.*
Denarie, J., and Debelle, F., "Rhizobium lipo-chitooligosaccharide nodulation factors: Signaling molecules mediating recognition and morphogenesis", Annual Review of Biochemistry 1996, vol. 65, pp. 503-535.*
van der Holst et al. 2001. Current Opinions in Structural Biology 11, 608-616.
Robina et al. 2002 Tetrahedron 58, 521-530.
Samain et al. 1999, Journal of Biotechnology 72, 33-47.
Samain et al 1997, Carbohydrate Research 302, 35-42.
Cottaz et al 2005, Metabolic Engineering 7, 311-317.
Dumon et al 2006, ChemBioChem 7, 359-365.
Denarie et al 1996, Annu. Rev. Biochem. 65, 503-535.
Khan et al 2002, Photosynthetica 40(4), 621-624.
Jung et al 2007, Carbohydrate Polymers 67, 256-259.
Yoshikawa et al 1993, Plant Cell Physiol. 34(8), 1163-1173.
Hamel et al 2010, Planta 232, 787-806.
Okada et al 2002, Plant Cell Physiol 43(5), 505-512.
Muller et al 2000, Plant Physiology 124, 733-739.
Prome et al 1998, Pure & Appl. Chem. 70(1), 55-60.
Newsmart webpage re COS, www.glucosamine-chitosan.com (2005).
Darvill et al 1992, Glycobiology 2(3), 181-198.
Cote et al 1994, Plant Molecular Biology 26, 1379-1411.
Kasprezewska 2003, Cellular & Molecular Biology Letters 8, 809-824.

(Continued)

*Primary Examiner* — Allison Fox
*Assistant Examiner* — Michelle F Paguio Frising
(74) *Attorney, Agent, or Firm* — Adam Rucker

(57) ABSTRACT

According to the present invention new isolates of *Bradyrhizobium japonicum* have been isolated and possess unique properties. These *Bradyrhizobia* are plant growth-promoting rhizobacterium (PGPR), possess superior tolerance/resistance to desiccation, and enhance the overall performance of leguminous plant growth.

17 Claims, 5 Drawing Sheets

(56) References Cited

OTHER PUBLICATIONS

Cote et al 1995, Physiologia Plantarum 93, 401-410.
Halford 2010, "Smoke Signals", Chemical & Engineering News 88(15), 1-3.
D'Haeze et al 2002, Glycobiology 12(6), 79R-105R.
Demont-Caulet et al 1999, Plant Physiology 120, 83-92.
Maillet et al 2011, Nature 469, 58-64.
Macchiavelli et al 2004, Journal of Experimental Botany 55(408), 2635-2640.
Spaink 2000, Annu. Rev. Micriobiol 54, 257-288.
Pochanavanich et al 2002, Letters in Applied Microbiology 35, 17-21.
Shaw et al 2006, Environmental Microbiology 8(11), 1867-1880.
Ralston et al 2005, Plant Physiology 137, 1375-1388.
Wakelin et al 2004, Biol Fertil Soils 40, 36-43.
Diaz et al 2000, Molecular Plant-Microbe Interactions 13(3), 268-276.
Hungria et al 1997, Soil Biol. Biochem. 29(5/6), 819-830.
Friesen et al 2005, Appl Microbiol Biotechnol 68, 397-404.
Ferguson et al 2003, J Plant Growth Regul 22, 47-72.
Collinge et al 1993, The Plant Journal 3(1), 31-40.
Leibovitch et al 2001, J Agronomy & Crop Science 187, 281-292.
Pederson presentation Iowa State University "Soybean Growth and Development", 2006.
Prithiviraj et al 2003, Planta 216, 437-445.
Staehelin et al 1994, Proc. Natl. Acad. Sci. USA 91, 2196-2200.
Cytryn et al, 2007, J Bacteriology, 189(19), 6751-6762.
Deaker et al., 2007, Soil Biology & Biochemistry 39 573-580.
Leprince et al, 2010, Plant Science 179 554-564.
Mabood et al, 2006, Field Crops Research, 95 412-419.
Mary et al, 1994, Soil Biol Biochem 26(9), 1125-1132.
Radwan et al, 2007, Intl J Phytoremediation 9, 475-486.
Streeter, 2003, J Appl Microbiol 95, 484-491.
Sugawara et al, 2010, Appl Environ Microbiol 76(4), 1071-1081.
Supanjani et al, 2006 Plant Physiology and Biochemistry, 44 866-872.
Zahran., 2001, Journal of Biotechnology, 91 143-153.

* cited by examiner

BRADYRHIZOBIUM STRAINS

CROSS-REFERENCE TO RELATED APPLICATIONS

This application claims the benefit under 35 U.S.C. 119 of U.S. provisional application No. 61/576,470 filed Dec. 16, 2011, the contents of which are fully incorporated herein by reference.

REFERENCE TO A DEPOSIT OF BIOLOGICAL MATERIAL

This application contains a reference to a deposit of biological material, which deposit is incorporated herein by reference. For complete information see Table 1.

FIELD OF THE INVENTION

The present invention relates to isolated *Bradyrhizobium* bacterium having enhanced characteristics, including but not limited to, enhanced desiccation resistance.

BACKGROUND OF THE INVENTION

In order to maintain healthy growth, plants must extract a variety of elements from the soil in which they grow. These elements include nitrogen and the so-called micro-nutrients (e.g., copper, iron and zinc), but many soils are deficient in such elements or they contain them only in forms which cannot be readily taken up by plants (it is generally believed that essential elements cannot be readily taken up by plants unless they are present in dissolved form in the soil). Nitrogen is an essential element for most plants as it plays a role in the synthesis of amino acids, proteins, nucleotides, nucleic acids, chlorophyll, co-enzymes and in the overall growth and health of the plant. To counteract such deficiencies, sources of the deficient elements are commonly applied to soils in order to improve growth rates and yields obtained from crop plants. For example, nitrate and/or ammonium are often added to soil to counteract a lack of available nitrogen.

In the field of crop science, it is well known that many cultivated crops require that the soil provide relatively large amounts of nitrogen to the plant. The notable exceptions to those plants requiring nitrogen via the soil are plants from the legume family.

Specifically, leguminous plants are unique from non-leguminous plants in their ability to fix atmospheric nitrogen into ammonia. The ability to fix atmospheric nitrogen into a useable nitrogen source for the plant obviates the need for the plant to obtain nitrogen from the soil. Nitrogen fixation, however, requires a symbiotic relationship between the leguminous plant and native bacterial within the soil. One of the most extensively studied partners in this symbiotic relationship is bacteria belonging to the genus *Bradyrhizobium* or *Rhizobium*. Gresshoff, P. (1999). *Identification of Plant Genes Involved in Plant-Microbe Interactions*. Stacey, G. & Keen, T. (Ed.), *Plant-Microbe Interactions* (4th ed.) (Ch. 6). St. Paul: APS Press.

Symbiosis is generally achieved through an exchange of complex bidirectional signaling between the plant and the microbe and the microbe and the plant. Typically, plant factors, such as flavonoids and flavonoid like substances, induce colonization of the bacteria into the root nodule of the leguminous plant. (Gresshoff, 1999). Once the bacteria have colonized the root nodule, the bacteria effect morphological changes in the plant, namely root hair curling and the development of a new root organ—the nodule. (Gresshoff, 1999). The nodule permits the establishment of a new physiological environment for the nodule inducing bacteria to differentiate into a nitrogen-fixing endosymbiont, or bacteriod, for the colonized plant. (Gresshoff, 1999).

In order to assist with the symbiotic exchange of bi-directional signaling between the plant and microbe, bacteria, such as *Bradyrhizobia* sp., are often coated on a seed. To prolong the viability of the microbe on the seed, it is desirable that the microbe be tolerant to desiccation and dry environmental conditions generally.

There remains a need for microbes with enhanced desiccation resistance.

SUMMARY OF THE INVENTION

Described herein are novel bacterial strains having enhanced desiccation resistance, especially when the novel strains are compared to its parental strain, e.g., *Bradyrhizobium* sp., parental strain USDA 532C. The inventors have isolated and tested a significant number of bacterial strains for their desiccation resistance properties.

As disclosed throughout, the isolated strains are strains of the genus *Bradyrhizobium* spp. In particular, the isolated strains are strains of *Bradyrhizobium japonicum*. Even more particularly, the isolated strains are isolated *Bradyrhizobium japonicum* strains selected from the group consisting of:

the strain having the deposit accession number NRRL B-50608;

the strain having the deposit accession number NRRL B-50609;

the strain having the deposit accession number NRRL B-50610;

the strain having the deposit accession number NRRL B-50611;

the strain having the deposit accession number NRRL B-50612, or a combination of at least two or more of the above deposited strains.

Also described herein are compositions comprising a carrier and one or more of the bacterial strains described herein. In an embodiment, the composition comprises one or more plant signal molecules. In one embodiment, the composition comprises at least one lipo-chitooligosaccharide (LCO). In another embodiment the composition comprises at least one chitooligosaccharide (CO). In still another embodiment, the composition comprises at least one flavonoid. In still yet another embodiment, the composition comprises jasmonic acid or a derivative thereof. In another embodiment, the composition comprises linoleic acid or a derivative thereof. In yet another embodiment, the composition comprises linolenic acid or a derivative thereof. In still yet another embodiment, the composition comprises a karrikin.

Further described herein is a method for enhancing the growth of a plant or plant part comprising contacting a plant or plant part with one or more with one or more of the bacterial strains described herein. The method comprises introducing into the soil an inoculum of one or more of the bacterial strains described herein. In another embodiment, the method comprises introducing into the soil an inoculum of one or more of the bacterial strains as a seed coating.

Also described herein is a method for enhancing nitrogen fixation in a plant(s) comprising growing a plant(s) in a soil that contains a one or more of the bacterial strains described herein. In one embodiment, the plant(s) is a leguminous plant(s), non-leguminous plant(s), or combinations thereof.

In another embodiment, the plant is a plant selected from the group consisting of soybean, bean, alfalfa, clover, corn, lettuce tomatoes, potatoes, cucumbers, and combinations thereof.

Further described herein are seeds coated with the bacterial strains described herein.

DETAILED DESCRIPTION OF THE INVENTION

The disclosed bacterial strains have been isolated and tested for their ability to solubilize phosphorous. This is described in detail in the "Examples" section provided below. The disclosed embodiments further relate to compositions, seed coatings, methods for increasing the availability of phosphorus for plant uptake from soil, and methods for increasing the phosphorus uptake in plants comprising growing the plants in a soil containing a phosphorus source.

DEFINITIONS

As used herein, the singular forms "a", "an" and "the" are intended to include the plural forms as well, unless the context clearly indicates otherwise.

As used herein, the term "biologically pure culture" is intended to mean a culture essentially free from biological contamination and having a genetic uniformity such that different subcultures taken therefrom will display substantially identical genotypes and phenotypes (e.g., cultures have a purity of at least 60%, of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, up to 100% pure).

As used herein, the term "isolate, isolates, isolating, and/or isolated, etc." is intended to mean that the referenced material is removed from the environment in which it is normally found.

As used herein, the term "inoculum" is intended to mean any form of bacterial cells, or spores, which is capable of propagating on or in the soil when the conditions of temperature, moisture, etc., are favorable for bacterial growth.

As used herein, the terms "spore" has its normal meaning which is well known and understood by those of skill in the art and generally refers to a microorganism in its dormant, protected state.

As used herein, the term "source" of a particular element is intended to mean a compound of that element which, at least in the soil conditions under consideration, does not make the element fully available for plant uptake.

As used herein, the terms "effective amount", "effective concentration", or "effective dosage" is intended to mean the amount, concentration, or dosage of the one or more bacterial isolates sufficient to cause an increase in the growth of a plant or plant part or an increase in nitrogen fixation. The actual effective dosage in absolute value depends on factors including, but not limited to, the size (e.g., the area, the total acreage, etc.) of the land for application with the bacterial isolates, synergistic or antagonistic interactions between the other active or inert ingredients which may increase or reduce activity of the bacterial isolates, and the stability of the bacterial isolates in compositions and/or as seed treatments. The "effective amount", "effective concentration", or "effective dosage" of the bacterial composition may be determined, e.g., by a routine dose response experiment.

As used herein, the terms "carrier" or "agronomically acceptable carrier" are intended to refer to any material which can be used to deliver the actives (e.g., a bacterial strain) to a seed, soil, plant or plant part.

As used herein, the term "soil-compatible carrier" is intended to refer to any material which can be added to a soil without causing/having an adverse effect on plant growth, soil structure, soil drainage, or the like.

As used herein, the term "seed-compatible carrier" is intended to refer to any material which can be added to a seed without causing/having an adverse effect on the seed, the plant that grows from the seed, seed germination, or the like.

As used herein, the term "agriculturally beneficial ingredient(s)" is intended to mean any agent or combination of agents capable of causing or providing a beneficial and/or useful effect in agriculture.

As used herein, "at least one biologically active ingredient" is intended to mean biologically active ingredients (e.g., signal molecules, other microorganisms, etc.) other than the one or more bacterial isolates described herein.

As used herein, the term "desiccation" is intended to mean a state of extreme dryness, e.g., conditions without moisture and/or water. The terms "desiccation resistance" and/or "desiccation tolerance" are intended to encompass the ability of an organism to withstand and/or survive and/or endure conditions of extreme dryness.

As used herein, terms "nitrogen fixation", "fixation of atmospheric nitrogen", or "nitrogen fixing", etc. are intended to encompass biological processes in which molecular nitrogen or nitrogen in the atmosphere is converted into one or more nitrogenous (N) compounds, including but not limited to, ammonia, ammonium salts, urea, and nitrates.

As used herein, the term "nitrogen fixing organism" is intended to refer to any organism (e.g., diazotrophs) capable of converting molecular nitrogen or nitrogen in the atmosphere into one or more nitrogenous (N) compounds, including but not limited to, ammonia, ammonium salts, urea, and nitrates.

As used herein, terms "phosphate solubilization", or "phosphate solubilizing", etc. are intended to mean the conversion of insoluble phosphate (e.g., rock phosphate, etc.) into a soluble phosphate form.

Figure 1:
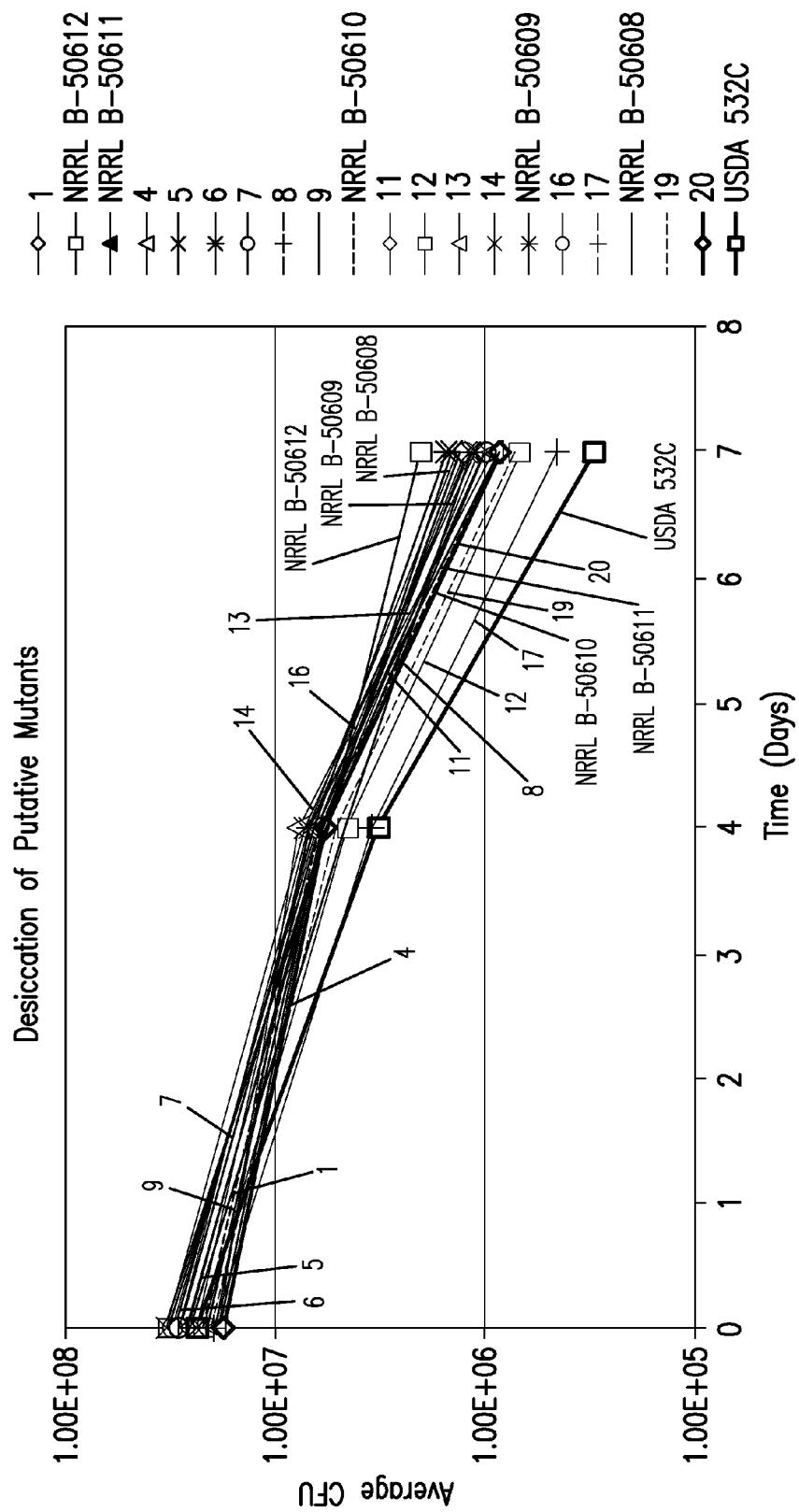
FIG. 1 is a graphical representation of the preliminary screening of desiccation resistant mutants compared when compared to the desiccation resistance of parental strain USDA 532C.

As used herein, the term "phosphate solubilizing organism" is intended to refer to any organism capable of converting insoluble phosphate into a soluble phosphate form.

As used herein, the terms "plant(s)" and "plant part(s)" are intended to refer to all plants and plant populations such as desired and undesired wild plants or crop plants (including naturally occurring crop plants). Crop plants can be plants, which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, nodules, tubers, and rhizomes. The plant parts also include harvested material and vegetative and generative propagation material (e.g., cuttings, tubers, rhizomes, off-shoots and seeds, etc.).

As used herein, the term "nodule" is intended to include, but not be limited to, determinate nodules, indeterminate nodules, or a combination thereof. Examples of determinate nodules and indeterminate nodules are well known in the art and described in Denison, R. F., 2000, *The Amer. Naturalist.* 156 (6): 567-576. Determinate nodules are found on *Glycine, Lotus,* or *Phaseolus* species and are round and spherical in shape. (Denison, 2000) Determinate nodules grow only for a limited period of time—typically a few weeks. (Denison, 2000) In contrast to determinate nodules, indeterminate nodules are found on *Medicago, Trifolium,* and *Pisium* species, have an elongated shape and grow continuously. (Denison, 2000) The term "nodule occupancy" is a term known in the art. McDermott T. R. & Graham, P. H., *Appl. and Environ. Microbiol.* 55(10): 2493-2498. It is well known in the art that, notwithstanding the rare exception, a single nodule will contain only one bacterial strain. Johnston, A. W. B., et al., 1974, *J. Gen. Microbiol* 87: 343-350; Dunham, D. H. & Baldwin, I. L., 1931, *Soil Science* 32: 235-249; Johnson, H. W., et al., 1963, *Agrono. J.* 55: 269-271; Dudman, W. F. & Brockwell, J., 1968, *J. Agricul. Res.* 19: 739-747; Nicol, H. & Thorton, H. G., 1941, *Proc. Roy. Soc. B* 130, 32-59; Hughes, D. Q., & Vincent, J. M., 1942, *Proc. of the Linnenan Soc. of New South Wales* 67: 142-152; and Vincent, J. M. & Waters, L. M., 1953, *J. Gen. Microbiol.* 9: 357-370.

As used herein, term "enhanced plant growth" is intended to refer to increased plant yield (e.g., increased biomass, increased fruit number, or a combination thereof as measured by bushels per acre), increased root number, increased root mass, increased root volume, increased leaf area, increased plant stand, increased plant vigor, increased weight of a plant (e.g. total dry weight of a plant or plant part, total fresh weight or a plant or plant part, etc.), or combinations thereof.

As used herein, "enhanced competitiveness" and/or "enhanced nodulation" is defined to mean bacterial strain(s) possessing a percent nodule occupancy, e.g. at least 50%, at least 55%, at least 60%, at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, up to 100% nodule occupancy.

As used herein, the term "temperature tolerance" is intended to mean the range of temperatures at which a bacterial strain(s) are able to grow, e.g., the maximum and minimum temperatures at which a bacterial strain can grow.

As used herein, the term "commercially available strain(s)" is intended to mean commercially available bacterial strains, e.g., USDA 532C, USDA 110, USDA 123, USDA 127, USDA 129, etc. Cregan, P. B., et al., 1989, *Appl. and Enviro. Microbiol.* 55 (10): 2532-2536.

As used herein, the term "micronutrient(s)" is intended to refer to nutrients which are needed for plant growth, plant health, and/or plant development.

As used herein, the term "biostimulant(s)" is intended to refer to any substance capable of enhancing metabolic or physiological processes within plants and soils.

As used herein, the term "wetting agent(s)" is intended to refer to any substance capable of lowering and/or reducing the surface tension of water.

Strains

In one embodiment, the isolated strain(s) described herein is a nitrogen fixing bacterial strain(s). In another embodiment, the strain(s) is a *Bradyrhizobum* sp. strain(s). In a further aspect, the strain is derived from a strain of *Bradyrhizobium*, including but not limited to a strain selected from the group consisting of *Bradyrhizobium* bete, *Bradyrhizobium* canariense, *Bradyrhizobium* elkanii, *Bradyrhizobium* iriomotense, *Bradyrhizobium* japonicum, *Bradyrhizobium* jicamae, *Bradyrhizobium* liaoningense, *Bradyrhizobium pachyrhizi*, and *Bradyrhizobium yuanmingense*. In yet another embodiment, the strain(s) is a *Bradyrhizobum japonicum* strain(s).

In yet another embodiment, the isolated strain(s) is a strain(s) of *Bradyrhizobium* sp. having enhanced/increased bacterial survival rate in a substantially moisture free environment when the survival rate of the isolated *Bradyrhizobium* strain(s) is compared to the survival rate of a parental strain(s), e.g., parental strain *Bradyrhizobium japonicum* USDA 532C, over a period of time, e.g., at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, at least 1 year or more.

In still another embodiment, the isolated strain(s) is a strain(s) of *Bradyrhizobium* sp. having an enhanced/increased survival rate in a substantially moisture free environment, wherein an increased survival rate in a substantially moisture free environment includes an increased bacterial survival rate in an environment that is at least 70% moisture free, e.g., at least 75%, at least 80%, at least 85%, at least 85%, at least 90%, at least 91%, at least 92%, at least 93%, at least 94%, at least 95%, at least 96%, at least 97%, at least 98%, at least 99%, up to a 100% moisture free environment, when the survival rate of the isolated *Bradyrhizobium* strain(s) is compared to the survival rate of a parental strain(s), e.g., parental strain *Bradyrhizobium japonicum* USDA 532C.

In another embodiment the isolated strain(s) is a strain(s) of *Bradyrhizobium* sp. having the following enhanced/superior characteristics when compared to commercially available strains, e.g., commercial strain *Bradyrhizobium japonicum* USDA 532C, wherein enhanced/superior characteristics include, but are not limited to:

a. enhanced competitiveness for colonizing a soybean plant; and b. enhanced effectiveness at promoting soybean plant growth.

In still another embodiment, the isolated strain(s) is a strain(s) of *Bradyrhizobium* sp. having enhanced/superior competitiveness for colonizing a plant. In yet another embodiment, the isolated strain(s) is a strain(s) of *Bradyrhizobium* sp. having enhanced/superior effectiveness at promoting plant growth. In still another embodiment, the isolated strain(s) is a strain(s) of *Bradyrhizobium* sp. having enhanced/superior competitiveness for colonizing a plant and enhanced/superior effectiveness at promoting plant growth.

In yet another aspect of the present invention, the isolated strain(s) is a strain(s) of *Bradyrhizobium* sp. having enhanced/superior temperature tolerance.

In still another aspect of the present invention, the isolated strain(s) is a strain(s) of *Bradyrhizobium* sp. having natural resistance to glyphosate.

In still another embodiment, the strains are *Bradyrhizobum japonicum* strains selected from the group consisting of:

the strain having the deposit accession number NRRL B-50608;

the strain having the deposit accession number NRRL B-50609;

the strain having the deposit accession number NRRL B-50610;

the strain having the deposit accession number NRRL B-50611; and the strain having the deposit accession number NRRL B-50612.

In a particular embodiment, the strain(s) may be one or more of the above mentioned deposited strains (e.g., including at least two of the above strains, at least three of the above strains, at least four of the above strains, up to and including all of the above strains).

In an embodiment, the strain is the strain having the deposit accession NRRL B-50608. In an embodiment, the strain is the strain having the deposit accession number NRRL B-50609. In an embodiment, the strain is the strain having the deposit accession number NRRL B-50610. In an embodiment, the strain is the strain having the deposit accession number NRRL B-50611. In an embodiment, the strain is the strain having the deposit accession number NRRL B-50612.

In another embodiment, the bacterial culture(s) has properties/characteristics identical to at least one of the deposited strains or a combination of at least two of the above deposited strains, including more than two, such as, at least three of the above strains, at least four of the above strains, up to and including all of the above strains. Properties/characteristics of the bacterial culture include, but are not limited to, bacterial strains having enhanced and/or superior resistance to desiccation. In still another embodiment, the strain(s) is a strain(s) of *Bradyrhizobium* having enhanced and/or superior desiccation resistance when the desiccation resistance is compared to the desiccation resistance and/or tolerance of a parental strain(s) of bacteria, e.g., parental strain *Bradyrhizobium japonicum* USDA 532C.

In another aspect, the isolated bacterial strain(s) of the present invention includes strain(s) that are closely related to any of the above strains on the basis of 16S rDNA sequence identity. See Stackebrandt E, et al., "Report of the ad hoc committee for the re-evaluation of the species definition in bacteriology," *Int J Syst Evol Microbiol*. 52(3):1043-7 (2002) regarding use of 16S rDNA sequence identity for determining relatedness in bacteria. In an embodiment, the at least one strain is at least 95% identical to any of the above strains on the basis of 16S rDNA sequence identity, at least 96% identical to any of the above strains on the basis of 16S rDNA sequence identity, at least 97% identical to any of the above strains on the basis of 16S rDNA sequence identity, at least 98% to any of the above strains on the basis of 16S rDNA sequence identity, at least 98.5% identical to any of the above strains on the basis of 16S rDNA sequence identity, at least 99% identical to any of the above strains on the basis of 16S rDNA sequence identity or at least 99.5% to any of the above strains on the basis of 16S rDNA sequence identity.

The *Bradyrhizobium bacterium* described herein, and in particular, the strains having deposit accession numbers NRRL B-50608, NRRL B-50609, NRRL B-50610, NRRL B-50611, and NRRL B-50612, can be grown according to methods known in the art.

The resulting material may be used directly in a composition, as a seed treatment, or the spores may be harvested, concentrated by centrifugation, formulated, and then dried using air drying, freeze drying, or fluid bed drying techniques (Friesen T., Hill G., Pugsley T., Holloway G., and Zimmerman D. 2005, Experimental determination of viability loss of *Penicillium bilaiae* conidia during convective air-drying Appl Microbiol Biotechnol 68: 397-404) to produce a wettable powder.

Above mentioned deposited strains were deposited on Nov. 30, 2011, as indicated in more details below in the "Materials & Methods"-section, under terms of the Budapest Treaty on the International Recognition of the Deposit of Microorganisms for the Purposes of Patent Procedure at Agricultural Research Culture Collection (NRRL), International Depositary Authority, 1815 N. University Street, Peoria, Ill. 61604, U.S.A.

Compositions:

In another aspect, the invention relates to a composition comprising a carrier and an inoculum of one or more of the deposited strains (either spore form or strains in a vegetative state) described herein. In certain embodiments, the composition may be in the form of a liquid, a slurry, a solid, or a powder (wettable powder or dry powder). In another embodiment, the composition may be in the form of a seed coating. Compositions in liquid, slurry, or powder (e.g., wettable powder) form may be suitable for coating seeds. When used to coat seeds, the composition may be applied to the seeds and allowed to dry. In embodiments wherein the composition is a powder (e.g., a wettable powder), a liquid, such as water, may need to be added to the powder before application to a seed. Example of yet other carriers include moistened bran, dried, sieved and applied to seeds prior coated with an adhesive, e.g., gum arabic.

Carriers:

The carriers described herein will allow the deposited bacterial strain(s) to remain efficacious (e.g., capable of fixing nitrogen) and viable once formulated. Non-limiting examples of carriers described herein include liquids, slurries, or solids (including wettable powders or dry powders). In an embodiment, the carrier is a soil compatible carrier as described herein.

In one embodiment, the carrier is a liquid carrier. Non-limiting examples of liquids useful as carriers for the compositions disclosed herein include water, an aqueous solution, or a non-aqueous solution. In one embodiment, the carrier is water. In another embodiment the carrier is an aqueous solution, such as sugar water. In another embodiment, the carrier is a non-aqueous solution. If a liquid carrier is used, the liquid (e.g., water) carrier may further include growth media to culture the deposited bacterial strains. Non-limiting examples of suitable growth media for the deposited bacterial strains include arabinose-gluconate (AG), yeast extract mannitol (YEM), G16 media, or any media known to those skilled in the art to be compatible with, and/or provide growth nutrients to the deposited bacterial strains.

In another embodiment, the carrier is a slurry. In an embodiment, the slurry may comprise a sticking agent, a liquid, or a combination thereof. It is envisioned that the sticking agent can be any agent capable of sticking the inoculum (e.g., one or more of the deposited strains) to a substrate of interest (e.g., a seed). Non-limiting examples of sticking agents include alginate, mineral oil, syrup, gum arabic, honey, methyl cellulose, milk, wallpaper paste, and combinations thereof. Non-limiting examples of liquids appropriate for a slurry include water or sugar water.

In another embodiment, the carrier is a solid. In a particular embodiment the solid is a powder. In one embodiment the powder is a wettable powder. In another embodiment, the powder is a dry powder. In another embodiment, the solid is a granule. Non-limiting examples of solids useful as carriers for the compositions disclosed herein include peat, wheat, wheat chaff, ground wheat straw, bran (e.g., moistened bran, non-moistened bran), vermiculite, cellulose, starch, soil (pasteurized or unpasteurized), gypsum, talc, clays (e.g., kaolin, bentonite, montmorillonite), and silica gels.

Optional Agriculturally Beneficial Ingredients:

The compositions disclosed herein may comprise one or more optional ingredients. Non-limiting examples of optional ingredients include one or more biologically active ingredients, micronutrients, biostimulants, preservatives, polymers, wetting agents, surfactants, or combinations thereof.

Biologically Active Ingredient(s):

The compositions described herein may optionally include one or more biologically active ingredients as described herein. Non-limiting examples of biologically active ingredients include signal molecules (e.g., lipo-chitooligosaccharides (LCO), chitooligosaccharides (CO), chitinous compounds, flavonoids, jasmonic acid or derivatives thereof, linoleic acid or derivatives thereof, linolenic acid or derivatives thereof, kerrikins, etc.) and beneficial microorganisms (e.g., Rhizobium spp., Bradyrhizobium spp., Sinorhizobium spp., Azorhizobium spp., etc.).

Signal Molecule(s):

In an embodiment, the compositions described herein include one or more signal molecules. In one embodiment, the one or more signal molecules are one or more LCOs. In another embodiment, the one or more signal molecules are one or more chitinous compounds. In still another embodiment, the one or more signal molecules are one or more COs. In yet another embodiment, the one or more signal molecules are one or more flavonoids or derivatives thereof. In still yet another embodiment, the one or more signal molecules are one or more non-flavonoid nod gene inducers (e.g., jasmonic acid, linoleic acid, linolenic acid, and derivatives thereof). In still yet another embodiment, the one or more signal molecules are one or more karrikins or derivatives thereof. In still another embodiment, the one or more signal molecules are one or more LCOs, one or more chitinous compounds, one or more COs, one or more flavonoids and derivatives thereof, one or more non-flavonoid nod gene inducers and derivatives thereof, one or more karrikins and derivatives thereof, or any signal molecule combination thereof.

LCOs:

Lipo-chitooligosaccharide compounds (LCDs), also known in the art as symbiotic Nod signals or Nod factors, consist of an oligosaccharide backbone of β-1,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. An example of an LCO is presented below as formula I:

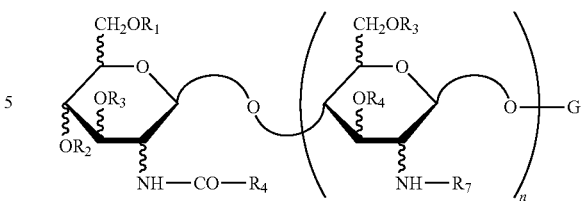

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO-$, $C_xH_y\,CO-$ where x is an integer between 0 and 17, and y is an integer between 1 and 35, or any other acyl group such as for example a carbamyl, $R_4$ represents a mono-, di- or triunsaturated aliphatic chain containing at least 12 carbon atoms, and n is an integer between 1 and 4.

LCOs may be obtained (isolated and/or purified) from bacteria such as Rhizobia, e.g., Rhizobium spp., Bradyrhizobium spp., Sinorhizobium spp. and Azorhizobium spp. LCO structure is characteristic for each such bacterial species, and each strain may produce multiple LCO's with different structures. For example, specific LCOs from S. meliloti have also been described in U.S. Pat. No. 5,549,718 as having the formula II:

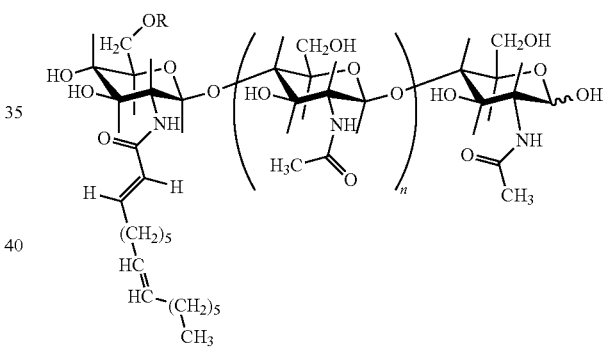

in which R represents H or $CH_3CO-$ and n is equal to 2 or 3.

Even more specific LCOs include NodRM, NodRM-1, NodRM-3. When acetylated (the R=$CH_3CO-$), they become AcNodRM-1, and AcNodRM-3, respectively (U.S. Pat. No. 5,545,718).

LCOs from Bradyrhizobium japonicum are described in U.S. Pat. Nos. 5,175,149 and 5,321,011. Broadly, they are pentasaccharide phytohormones comprising methylfucose. A number of these B. japonicum-derived LCOs are described: BjNod-V ($C_{18:1}$); BjNod-V ($A_C$, $C_{18:1}$), BjNod-V ($C_{16:1}$); and BjNod-V ($A_C$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

LCOs used in compositions of the invention may be obtained (i.e., isolated and/or purified) from bacterial strains that produce LCO's, such as strains of Azorhizobium, Bradyrhizobium (including B. japonicum), Mesorhizobium, Rhizobium (including R. leguminosarum), Sinorhizobium (including S. meliloti), and bacterial strains genetically engineered to produce LCO's.

Also encompassed by the present invention are compositions using LCOs obtained (i.e., isolated and/or purified) from a mycorrhizal fungus, such as fungi of the group Glomerocycota, e.g., *Glomus intraradicus*. The structures of representative LCOs obtained from these fungi are described in WO 2010/049751 and WO 2010/049751 (the LCOs described therein also referred to as "Myc factors").

Further encompassed by compositions of the present invention is use of synthetic LCO compounds, such as those described in WO 2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present invention) for the construction of LCOs may also be synthesized by genetically engineered organisms, e.g., as in Samain, et al., Carb. Res. 302:35-42 (1997); Samain, et al., J. Biotechnol. 72:33-47 (1999).

LCO's may be utilized in various forms of purity and may be used alone or in the form of a culture of LCO-producing bacteria or fungi. Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage.

COs:

Chitooligosaccharides (COs) are known in the art as β-1-4 linked N acetyl glucosamine structures identified as chitin oligomers, also as N-acetylchitooligosaccharides. CO's have unique and different side chain decorations which make them different from chitin molecules [$(C_8H_{13}NO_5)$n, CAS No. 1398-61-4], and chitosan molecules [$(C_5H_{11}NO_4)$n, CAS No. 9012-76-4]. Representative literature describing the structure and production of COs is as follows: Van der Hoist, et al., Current Opinion in Structural Biology, 11:608-616 (2001); Robina, et al., Tetrahedron 58:521-530 (2002); Hanel, et al., Planta 232:787-806 (2010); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (Sep. 21, 2000); and Demont-Caulet, et al., Plant Physiol. 120(1):83-92 (1999). The COs may be synthetic or recombinant. Methods for preparation of recombinant COs are known in the art. See, e.g., Samain, et al. (supra.); Cottaz, et al., Meth. Eng. 7(4):311-7 (2005) and Samain, et al., J. Biotechnol. 72:33-47 (1999).

Chitinous Compounds:

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), and chitosan, (IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2 (hydroxymethyl)oxane-3,4-diol).

These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965,545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids:

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include chalcones, anthocyanidins, coumarins, flavones, flavanols, flavonols, flavanones, and isoflavones. See, Jain, et al., J. Plant Biochem. & Biotechnol. 11:1-10 (2002); Shaw, et al., Environmental Microbiol. 11:1867-80 (2006).

Representative flavonoids that may be useful in compositions of the present invention include luteolin, apigenin, tangeritin, quercetin, kaempferol, myricetin, fisetin, isorhamnetin, pachypodol, rhamnazin, hesperetin, naringenin, formononetin, eriodictyol, homoeriodictyol, taxifolin, dihydroquercetin, dihydrokaempferol, genistein, daidzein, glycitein, catechin, gallocatechin, catechin 3-gallate, gallocatechin 3-gallate, epicatechin, epigallocatechin, epicatechin 3-gallate, epigallocatechin 3-gallate, cyaniding, delphinidin, malvidin, pelargonidin, peonidin, petunidin, or derivatives thereof. Flavonoid compounds are commercially available, e.g., from Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston, et al., Plant Physiology 137:1375-88 (2005).

Non-Flavonoid Nod-Gene Inducer(s):

Jasmonic acid (JA, [1R-[1α,2β(Z)]]-3-oxo-2-(pentenyl) cyclopentaneacetic acid) and its derivatives, linoleic acid ((Z,Z)-9,12-Octadecadienoic acid) and its derivatives, and linolenic acid ((Z,Z,Z)-9,12,15-octadecatrienoic acid) and its derivatives, may also be used in compositions of the present invention. Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibbrella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Jasmonates, linoleic acid and linoleic acid (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001; and Mabood, Fazli, "Linoleic and linolenic acid induce the expression of nod genes in *Bradyrhizobium japonicum*," USDA 3, May 17, 2001.

Useful derivatives of linoleic acid, linolenic acid, and jasmonic acid that may be useful in compositions of the present invention include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikin(s):

Karrikins are vinylogous 4H-pyrones e.g., 2H-furo[2,3-c]pyran-2-ones including derivatives and analogues thereof. Examples of these compounds are represented by the following structure:

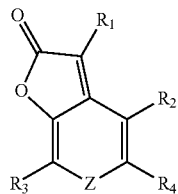

wherein; Z is O, S or NR$_5$; R$_1$, R$_2$, R$_3$, and R$_4$ are each independently H, alkyl, alkenyl, alkynyl, phenyl, benzyl, hydroxy, hydroxyalkyl, alkoxy, phenyloxy, benzyloxy, CN, COR$_6$, COOR=, halogen, NR$_6$R$_7$, or NO$_2$; and R$_5$, R$_6$, and R$_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present invention include the following: 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R4=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH$_3$), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H), 3,6-dimethylfuro[2,3-c]pyridin-2(6H)-one (where Z=N—CH$_3$, R$_1$=CH$_3$, R$_2$, R$_3$, R$_4$=H). See, U.S. Pat. No. 7,576,213. These molecules are also known as karrikins. See, Halford, "Smoke Signals," in Chem. Eng. News (Apr. 12, 2010), at pages 37-38 (reporting that karrikins or butenolides which are contained in smoke act as growth stimulants and spur seed germination after a forest fire, and can invigorate seeds such as corn, tomatoes, lettuce and onions that had been stored). These molecules are the subject of U.S. Pat. No. 7,576,213.

Beneficial Microorganism(s):

In an embodiment, the compositions described herein may comprise one or more beneficial microorganisms. The one or more beneficial microorganisms may have one or more beneficial properties (e.g., produce one or more of the signal molecules described herein, enhance nutrient and water uptake, enhance growth, enhance seed germination, enhance seedling emergence, break the dormancy or quiescence of a plant, etc.).

In one embodiment, the beneficial microorganism(s) comprise one or more bacteria that produce one or more of the signal molecules described herein. In still another embodiment, the bacteria are bacteria from the genera *Rhizobium* spp. (e.g., *R. cellulosilyticum, R. daejeonense, R. etli, R. galegae, R. gallicum, R. giardinii, R. hainanense, R. huautlense, R. indigoferae, R. leguminosarum, R. loessense, R. lupini, R. lusitanum, R. meliloti, R. mongolense, R. miluonense, R. sullae, R. tropici, R. undicola*, and/or *R. yanglingense*), *Azorhizobium* spp. (e.g., *A. caulinodans* and/or *A. doebereinerae*), *Sinorhizobium* spp. (e.g., *S. abri, S. adhaerens, S. americanum, S. aboris, S. fredii, S. indiaense, S. kostiense, S. kummerowiae, S. medicae, S. meliloti, S. mexicanus, S. morelense, S. saheli, S. terangae*, and/or *S. xinjiangense*), *Mesorhizobium* spp., (*M. albiziae, M. amorphae, M. chacoense, M. ciceri, M. huakuii, M. loti, M. mediterraneum, M. pluifarium, M. septentrionale, M. temperatum*, and/or *M. tianshanense*), and combinations thereof. In a particular embodiment, the beneficial microorganism is selected from the group consisting of *R leguminosarum, R meliloti, S. meliloti*, and combinations thereofIn another embodiment, the beneficial microorganism is *R leguminosarum*. In another embodiment, the beneficial microorganism is *R. meliloti*. In another embodiment, the beneficial microorganism is *S. meliloti*.

In another embodiment, the one or more beneficial microorganisms comprise one or more phosphate solubilizing microorganisms. Phosphate solubilizing microorganisms include fungal and bacterial strains. In an embodiment, the phosphate solubilizing microorganism includes species from a genus selected from the group consisting of *Acinetobacter* spp. (e.g., *Acinetobacter calcoaceticus*, etc.), *Arthrobacter* spp, *Arthrobotrys* spp. (e.g., *Arthrobotrys oligospora*, etc.), *Aspergillus* spp. (e.g., *Aspergillus niger*, etc.), *Azospirillum* spp. (e.g., *Azospirillum halopraeferans*, etc.), *Bacillus* spp. (e.g., *Bacillus amyloliquefaciens, Bacillus atrophaeus, Bacillus circulans, Bacillus licheniformis, Bacillus subtilis*, etc.), *Burkholderia* spp. (e.g., *Burkholderia cepacia, Burkholderia vietnamiensis*, etc.), *Candida* spp. (e.g., *Candida krissii*, etc.), *Chryseomonas* spp. (e.g., *Chryseomonas luteola*, etc.), *Enterobacter* spp. (e.g., *Enterobacter aerogenes, Enterobacter asburiae, Enterobacter* spp., *Enterobacter taylorae*, etc.), *Eupenicillium* spp. (e.g., *Eupenicillium parvum*, etc.), *Exiguobacterium* spp., *Klebsiella* spp., *Kluyvera* spp. (e.g., *Kluyvera cryocrescens*, etc.), *Microbacterium* spp., *Mucor* spp. (e.g., *Mucor ramosissimus*, etc.), *Paecilomyces* spp. (e.g., *Paecilomyces hepialid, Paecilomyces marquandii*, etc.), *Paenibacillus* spp. (e.g., *Paenibacillus macerans, Paenibacillus mucilaginosus*, etc.), *Penicillium* spp. (e.g., *Penicillium bilaiae* (formerly known as *Penicillium bilaii*), *Penicillium albidum, Penicillium aurantiogriseum, Penicillium chrysogenum, Penicillium citreonigrum, Penicillium citrinum, Penicillium digitatum, Penicillium frequentas, Penicillium fuscum, Penicillium gaestrivorus, Penicillium glabrum, Penicillium griseofulvum, Penicillium implicatum, Penicillium janthinellum, Penicillium lilacinum, Penicillium minioluteum, Penicillium montanense, Penicillium nigricans, Penicillium oxalicum, Penicillium pinetorum, Penicillium pinophilum, Penicillium purpurogenum, Penicillium radicans, Penicillium radicum, Penicillium raistrickii, Penicillium rugulosum, Penicillium simplicissimum, Penicillium solitum, Penicillium variabile, Penicillium velutinum, Penicillium viridicatum, Penicillium glaucum, Penicillium fussiporus*, and *Penicillium expansum*, etc.), *Pseudomonas* spp. (e.g., *Pseudomonas corrugate, Pseudomonas fluorescens, Pseudomonas lutea, Pseudomonas poae, Pseudomonas putida, Pseudomonas stutzeri, Pseudomonas trivialis*, etc.), *Serratia* spp. (e.g., *Serratia marcescens*, etc.), *Stenotrophomonas* spp. (e.g., *Stenotrophomonas maltophilia*, etc.), *Streptomyces* spp., *Streptosporangium* spp., *Swaminathania* spp. (e.g., *Swaminathania salitolerans*, etc.), *Thiobacillus* spp. (e.g., *Thiobacillus ferrooxidans*, etc.), *Torulospora* spp. (e.g., *Torulospora globosa*, etc.), *Vibrio* spp. (e.g., *Vibrio proteolyticus*, etc.), *Xanthobacter* spp. (e.g., *Xanthobacter agilis*, etc.), *Xanthomonas* spp. (e.g., *Xanthomonas campestris*, etc.), and combinations thereof.

In a particular embodiment, the one or more phosphate solubilizing microorganisms is a strain of the fungus *Penicillium*. In another embodiment, the one or more *Penicillium* species is *P. bilaiae, P. gaestrivorus*, or combinations thereof.

In another embodiment the beneficial microorganism is one or more mycorrhiza. In particular, the one or more mycorrhiza is an endomycorrhiza (also called vesicular arbuscular mycorrhizas, VAMs, arbuscular mycorrhizas, or AMs), an ectomycorrhiza, or a combination thereof.

In one embodiment, the one or more mycorrhiza is an endomycorrhiza of the phylum *Glomeromycota* and genera *Glomus* and *Gigaspora*. In still a further embodiment, the endomycorrhiza is a strain of *Glomus aggregatum, Glomus brasilianum, Glomus clarum, Glomus deserticola, Glomus etunicatum, Glomus fasciculatum, Glomus intraradices, Glomus monosporum*, or *Glomus mosseae, Gigaspora margarita*, or a combination thereof.

In another embodiment, the one or more mycorrhiza is an ectomycorrhiza of the phylum *Basidiomycota, Ascomycota*, and *Zygomycota*. In still yet another embodiment, the ectomycorrhiza is a strain of *Laccaria bicolor, Laccaria laccata, Pisolithus tinctorius, Rhizopogon amylopogon, Rhizopogon fulvigleba, Rhizopogon luteolus, Rhizopogon villosuli, Scleroderma cepa, Scleroderma citrinum*, or a combination thereof.

In still another embodiment, the one or more mycorrhiza is an ecroid mycorrhiza, an arbutoid mycorrhiza, or a monotropoid mycorrhiza. Arbuscular and ectomycorrhizas form ericoid mycorrhiza with many plants belonging to the order Ericales, while some Ericales form arbutoid and monotropoid mycorrhizas. All orchids are mycoheterotrophic at some stage during their lifecycle and form orchid mycorrhizas with a range of basidiomycete fungi. In one embodiment, the mycorrhiza may be an ericoid mycorrhiza, preferably of the phylum *Ascomycota*, such as *Hymenoscyphous ericae* or *Oidiodendron* sp. In another embodiment, the mycorrhiza also may be an arbutoid mycorrhiza, preferably of the phylum *Basidiomycota*. In yet another embodiment, the mycorrhiza may be a monotripoid mycorrhiza, preferably of the phylum *Basidiomycota*. In still yet another embodiment, the mycorrhiza may be an orchid mycorrhiza, preferably of the genus *Rhizoctonia*.

Micronutrient(s):

In still another embodiment, the compositions described herein may comprise one or more beneficial micronutrients. Non-limiting examples of micronutrients for use in the compositions described herein include vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), organic acids (e.g., acetic acid, citric acid, lactic acid, malic aclid, taurine, etc.), and combinations thereof. In a particular embodiment, the compositions may comprise phosphorous, boron, chlorine, copper, iron, manganese, molybdenum, zinc or combinations thereof.

In certain embodiments, where the compositions described herein may comprise phosphorous, it is envisioned that any suitable source of phosphorous may be provided. In one embodiment, the phosphorus may be derived from a source. In another embodiment, suitable sources of phosphorous include phosphorous sources capable of solubilization by one or more microorganisms (e.g., *Penicillium bilaiae*, etc.).

In one embodiment, the phosphorus may be derived from a rock phosphate source. In another embodiment the phosphorous may be derived from fertilizers comprising one or more phosphorous sources. Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In still another embodiment, the phosphorous may be derived from an organic phosphorous source. In a further particular embodiment, the source of phosphorus may include an organic fertilizer. An organic fertilizer refers to a soil amendment derived from natural sources that guarantees, at least, the minimum percentages of nitrogen, phosphate, and potash. Non-limiting examples of organic fertilizers include plant and animal by-products, rock powders, seaweed, inoculants, and conditioners. These are often available at garden centers and through horticultural supply companies. In particular the organic source of phosphorus is from bone meal, meat meal, animal manure, compost, sewage sludge, or guano, or combinations thereof.

In still another embodiment, the phosphorous may be derived from a combination of phosphorous sources including, but not limited to, rock phosphate, fertilizers comprising one or more phosphorous sources (e.g., monoammonium phosphate, diammonium phosphate, monocalcium phosphate, super phosphate, triple super phosphate, ammonium polyphosphate, etc.) one or more organic phosphorous sources, and combinations thereof.

Biostimulant(s):

In one embodiment, the compositions described herein may comprise one or more beneficial biostimulants. Biostimulants may enhance metabolic or physiological processes such as respiration, photosynthesis, nucleic acid uptake, ion uptake, nutrient delivery, or a combination thereof. Non-limiting examples of biostimulants include seaweed extracts (e.g., ascophyllum nodosum), humic acids (e.g., potassium humate), fulvic acids, myo-inositol, glycine, and combinations thereof. In another embodiment, the compositions comprise seaweed extracts, humic acids, fulvic acids, myo-inositol, glycine, and combinations thereof.

Polymer(s):

In one embodiment, the compositions described herein may further comprise one or more polymers. Non-limiting uses of polymers in the agricultural industry include agrochemical delivery, heavy metal removal, water retention and/or water delivery, and combinations thereof. Pouci, et al., Am. J. Agri. & Biol. Sci., 3(1):299-314 (2008). In one embodiment, the one or more polymers is a natural polymer (e.g., agar, starch, alginate, pectin, cellulose, etc.), a synthetic polymer, a biodegradable polymer (e.g., polycaprolactone, polylactide, poly (vinyl alcohol), etc.), or a combination thereof.

For a non-limiting list of polymers useful for the compositions described herein, see Pouci, et al., Am. J. Agri. & Biol. Sci., 3(1):299-314 (2008). In one embodiment, the compositions described herein comprise cellulose, cellulose derivatives, methylcellulose, methylcellulose derivatives, starch, agar, alginate, pectin, polyvinylpyrrolidone, and combinations thereof.

Wetting Agent(s):

In one embodiment, the compositions described herein may further comprise one or more wetting agents. Wetting agents are commonly used on soils, particularly hydrophobic soils, to improve the infiltration and/or penetration of water into a soil. The wetting agent may be an adjuvant, oil, surfactant, buffer, acidifier, or combination thereof. In an embodiment, the wetting agent is a surfactant. In an embodiment, the wetting agent is one or more nonionic surfactants, one or more anionic surfactants, or a combination thereof. In yet another embodiment, the wetting agent is one or more nonionic surfactants.

Surfactants suitable for the compositions described herein are provided in the "Surfactants" section.

Surfactant(s):

Surfactants suitable for the compositions described herein may be non-ionic surfactants (e.g., semi-polar and/or anionic and/or cationic and/or zwitterionic). It is envisioned that the surfactant(s) will cause as little harm to the activity of the one or more deposited strains and/or the one or more beneficial microorganisms as possible. The surfactants can wet and emulsify soil(s) and/or dirt(s). It is envisioned that the surfactants used in described composition have low toxicity for the microorganisms contained within the formulation. It is further envisioned that the surfactants used in the described composition have a low phytotoxicity (i.e., the degree of toxicity a substance or combination of substances has on a plant). A single surfactant or a blend of several surfactants can be used.

Anionic Surfactants

Anionic surfactants or mixtures of anionic and nonionic surfactants may also be used in the compositions. Anionic surfactants are surfactants having a hydrophilic moiety in an anionic or negatively charged state in aqueous solution. The compositions described herein may comprise one or more anionic surfactants. The anionic surfactant(s) may be either water soluble anionic surfactants, water insoluble anionic surfactants, or a combination of water soluble anionic surfactants and water insoluble anionic surfactants. Non-limiting examples of anionic surfactants include sulfonic acids, sulfuric acid esters, carboxylic acids, and salts thereof. Non-limiting examples of water soluble anionic surfactants include alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, alkyl carboxylates, or a combination thereof.

Nonionic Surfactants

Nonionic surfactants are surfactants having no electrical charge when dissolved or dispersed in an aqueous medium. In at least one embodiment of the composition described herein, one or more nonionic surfactants are used as they provide the desired wetting and emulsification actions and do not significantly inhibit spore stability and activity. The nonionic surfactant(s) may be either water soluble nonionic surfactants, water insoluble nonionic surfactants, or a combination of water soluble nonionic surfactants and water insoluble nonionic surfactants.

Water Insoluble Nonionic Surfactants

Non-limiting examples of water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, or combinations thereof. Also included are EO/PO block copolymers (EO is ethylene oxide, PO is propylene oxide), EO polymers and copolymers, polyamines, and polyvinylpynolidones.

Water Soluble Nonionic Surfactants

Non-limiting examples of water soluble nonionic surfactants include sorbitan fatty acid alcohol ethoxylates and sorbitan fatty acid ester ethoxylates.

Combination of Nonionic Surfactants

In one embodiment, the compositions described herein comprise at least one or more nonionic surfactants. In one embodiment, the compositions comprise at least one water insoluble nonionic surfactant and at least one water soluble nonionic surfactant. In still another embodiment, the compositions comprise a combination of nonionic surfactants having hydrocarbon chains of substantially the same length.

Other Surfactants

In another embodiment, the compositions described herein may also comprise organosilicone surfactants, silicone-based antifoams used as surfactants in silicone-based and mineral-oil based antifoams. In yet another embodiment, the compositions described herein may also comprise alkali metal salts of fatty acids (e.g., water soluble alkali metal salts of fatty acids and/or water insoluble alkali metal salts of fatty acids).

Herbicide(s):

In one embodiment, the compositions described herein may further comprise one or more herbicides. In a particular embodiment, the herbicide may be a pre-emergent herbicide, a post-emergent herbicide, or a combination thereof.

Suitable herbicides include chemical herbicides, natural herbicides (e.g., bioherbicides, organic herbicides, etc.), or combinations thereof. Non-limiting examples of suitable herbicides include bentazon, acifluorfen, chlorimuron, lactofen, clomazone, fluazifop, glufosinate, glyphosate, sethoxydim, imazethapyr, imazamox, fomesafe, flumiclorac, imazaquin, clethodim, pendimethalin; 3,4-Dimethyl-2,6-dinitro-N-pentan-3-yl-aniline; N-(1-ethylpropyl)-2,6-dinitro-3,4-xylidine; pronamide; propyzamide; 3,5-Dichloro-N-(1,1-dimethylpropynyl)benzamide; 3,5-Dichloro-N-(1,1-dimethyl-2-propynyl)benzamide; N-(1,1-Dimethylpropynyl)-3,5-dichlorobenzamide; S-ethyl N-ethylthiocyclohexanecarbamate; trifluralin; 2,6-Dinitro-N,N-dipropyl-4-(trifluoromethyl) aniline; glyphosate; N-(phosphonomethyl)glycine; and derivatives thereof. In one embodiment, the one or more herbicides for use in accordance with this disclosure include pronamide (commercially referred to as Kerb®); propyzamide; 3,5-Dichloro-N-(1,1-dimethylpropynyl)benzamide; 3,5-Dichloro-N-(1,1-dimethyl-2-propynyl)benzamide; N-(1, 1-Dimethylpropynyl)-3,5-dichlorobenzamide; cycloate, S-ethyl N-ethylthiocyclohexanecarbamate (commercially referred to as Ro-Neet®); trifluralin; 2,6-Dinitro-N,N-dipropyl-4-(trifluoromethyl)aniline; glyphosate; N-(phosphonomethyl)glycine; and derivatives thereof. Commercial products containing each of these compounds are readily available. Herbicide concentration in the composition will generally correspond to the labeled use rate for a particular herbicide.

Fungicide(s):

In one embodiment, the compositions described herein may further comprise one or more fungicides. Fungicides useful to the compositions described herein will suitably exhibit activity against a broad range of pathogens, including but not limited to *Phytophthora, Rhizoctonia, Fusarium, Pythium, Phomopsis* or *Selerotinia* and *Phakopsora* and combinations thereof.

Non-limiting examples of commercial fungicides which may be suitable for the compositions disclosed herein include PROTÉGÉ, RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAPTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides are most suitably used in accordance with the manufacturer's instructions at the recommended concentrations.

Insecticide(s):

In one embodiment, the compositions described herein may further comprise one or more insecticides. Insecticides useful to the compositions described herein will suitably exhibit activity against a broad range of insects including, but not limited to, wireworms, cutworms, grubs, corn rootworm, seed corn maggots, flea beetles, chinch bugs, aphids, leaf beetles, stink bugs, and combinations thereof.

Non-limiting examples of commercial insecticides which may be suitable for the compositions disclosed herein include CRUISER (Syngenta, Wilmington, Del.), GAUCHO and PONCHO (Gustafson, Plano, Tex.). Active ingredients in these and other commercial insecticides include thiamethoxam, clothianidin, and imidacloprid. Commercial insecticides are most suitably used in accordance with the manufacturer's instructions at the recommended concentrations.

Methods

In another aspect, methods of using the deposited strains and compositions described herein are disclosed.

In one embodiment a method for enhancing plant growth is described. The method comprises contacting a plant or plant part with an inoculum of one or more bacterial strains selected from the group consisting of:

the strain having the deposit accession number NRRL B-50608;

the strain having the deposit accession number NRRL B-50609;

the strain having the deposit accession number NRRL B-50610;

the strain having the deposit accession number NRRL B-50611;

the strain having the deposit accession number NRRL B-50612; or a mixture of two or more of the strains.

In a particular embodiment, the inoculum may comprise one or more of the above mentioned deposited strains (e.g., including at least two of the above strains, at least three of the above strains, at least four of the above strains, up to and including all of the above strains).

In an embodiment, the inoculum comprises the strain having the deposit accession number NRRL B-50608. In an embodiment, the inoculum comprises the strain having the deposit accession number NRRL B-50609. In an embodiment, the inoculum comprises the strain having the deposit accession number NRRL B-50610. In an embodiment, the inoculum comprises the strain having the deposit accession number NRRL B-50611. In an embodiment, the inoculum comprises the strain having the deposit accession number NRRL B-50612.

In still another embodiment, the step of contacting a plant or plant part with an inoculum of one or more of the deposited bacterial strains comprises contacting a plant or plant part with one or more of the compositions described herein. The inoculum(s) or compositions may be made to contact the plant or plant part according to methods known to those skilled in the art. Non-limiting examples include in-furrow introduction, coating seeds, etc. In a particular embodiment, the contacting step comprises in-furrow introduction of the inoculum or compositions described herein. In a particular embodiment, the contacting step comprises on-seed (seed coating) introduction of the inoculum or compositions described herein.

In certain embodiments, the step of contacting a plant or plant part with an inoculum of one or more of the deposited bacterial strains comprises introducing the inoculum into the soil in an amount of $1\times10^1$-$1\times10^8$, more preferably $1\times10^6$-$1\times10^{12}$ colony forming units per hectare. In other certain embodiments, the step of contacting a plant or plant part with an inoculum of one or more of the deposited bacterial strains comprises introducing the deposited bacterial strains as a seed coated with $1\times10^1$-$1\times10^8$, more preferably $1\times10^2$-$1\times10^6$ colony forming units per seed.

In another aspect, the method comprises growing plants in a soil comprising one or more of the bacterial strain. The method comprises:
  a) treating the soil an inoculum of one or more bacterial strains selected from the group consisting of:
    the strain having the deposit accession number NRRL B-50608;
    the strain having the deposit accession number NRRL B-50609;
    the strain having the deposit accession number NRRL B-50610;
    the strain having the deposit accession number NRRL B-50611;
    the strain having the deposit accession number NRRL B-50612; or a mixture of two or more of the strains; and
  b) growing a plant in the treated soil.

In a particular embodiment, the inoculum may comprise one or more of the above mentioned deposited strains (e.g., including at least two of the above strains, at least three of the above strains, at least four of the above strains, up to and including all of the above strains).

In an embodiment, the inoculum comprises the strain having the deposit accession number NRRL B-50608. In an embodiment, the inoculum comprises the strain having the deposit accession number NRRL B-50609. In an embodiment, the inoculum comprises the strain having the deposit accession number NRRL B-50610. In an embodiment, the inoculum comprises the strain having the deposit accession number NRRL B-50611. In an embodiment, the inoculum comprises the strain having the deposit accession number NRRL B-50612.

The step of treating the soil with an inoculum of one or more of the deposited bacterial strains comprises treating the soil with one or more of the compositions described herein. The inoculum(s) or compositions may be introduced into the soil according to methods known to those skilled in the art. Non-limiting examples include in-furrow treatment, coating seeds, etc. In a particular embodiment, the treating step comprises in-furrow treatment of the inoculum or compositions described herein. In a particular embodiment, the treating step comprises on-seed (seed coating)treatment of the inoculum or compositions described herein.

In a particular embodiment, the step of treating the soil with an inoculum of one or more of the deposited bacterial strains comprises treating the soil with one or more of the compositions described herein. In certain embodiments, the step of treating the soil with an inoculum of one or more of the deposited bacterial strains comprises treating the soil with an inoculum in an amount of $1\times10^1$-$1\times10^8$, more preferably $1\times10^6$-$1\times10^{12}$ colony forming units per hectare. In other certain embodiments, the step of treating the soil with an inocu-lum of one or more of the deposited bacterial strains comprises introducing the deposited bacterial strains as a seed coated with $1\times10^1$-$1\times10^8$, more preferably $1\times10^2$-$1\times10^6$ colony forming units per seed.

In another embodiment, the method further comprises the step of planting a plant or plant part. The planting step can occur before, after or during the treating step. In one embodiment, the planting step occurs before the treating step. In another embodiment, the planting step occurs during the treating step (e.g., the planting step occurs simultaneously with the treating step, the planting step occurs substantially simultaneous with the treating step, etc.). In still another embodiment, the planting step occurs after the treating step.

In another embodiment, the method further comprises the step of subjecting the soil to one or more agriculturally beneficial ingredients described herein. In one embodiment, the step of subjecting the soil to one or more agriculturally beneficial ingredients occurs before, during, after, or simultaneously with the treating step. In one embodiment, the step of subjecting the soil to one or more agriculturally beneficial ingredients as described herein occurs before the treating step. In another embodiment, the step of subjecting the soil to one or more agriculturally beneficial ingredients as described herein occurs during the treating step. In still another embodiment, the step of subjecting the soil to one or more agriculturally beneficial ingredients as described herein occurs after the treating step. In yet another embodiment, the step of subjecting the soil to one or more agriculturally beneficial ingredients as described herein occurs simultaneously with the treating step (e.g., treating the soil with one or more of the compositions described herein, etc.).

In yet another embodiment, the invention includes a method for treating seeds comprising applying to the seeds an inoculum of one or more bacterial strains selected from the group consisting of:
  the strain having the deposit accession number NRRL B-50608;
  the strain having the deposit accession number NRRL B-50609;
  the strain having the deposit accession number NRRL B-50610;
  the strain having the deposit accession number NRRL B-50611;
  the strain having the deposit accession number NRRL B-50612; or a mixture of two or more of the strains.

In a particular embodiment, the method for treating seeds may comprise one or more of the above mentioned deposited strains (e.g., including at least two of the above strains, at least three of the above strains, at least four of the above strains, up to and including all of the above strains).

In an embodiment, the method of treating seeds comprises applying to the seed the strain having the deposit accession number NRRL B-50608. In an embodiment, the method of treating seeds comprises applying to the seed the strain having the deposit accession number NRRL B-50609. In an embodiment, the method of treating seeds comprises applying to the seed the strain having the deposit accession number NRRL B-50610. In an embodiment, the method of treating seeds comprises applying to the seed the strain having the deposit accession number NRRL B-50611. In an embodiment, the method of treating seeds comprises applying to the seed the strain having the deposit accession number NRRL B-50612.

In yet another embodiment, the method further comprises the step of applying to the seeds one or more agriculturally beneficial ingredients to the seed. In another embodiment, the method comprises applying to the seeds any of the compositions described herein to the seeds.

In still another embodiment, the method comprises storing seeds with an inoculum of at least one or more of the isolated bacterial strains in a substantially moisture free environment for a period of time, e.g., at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, at least 1 year or more. In one aspect of the method, the seeds are leguminous plant seeds. In another aspect, the leguminous plant seeds are soybean seeds.

The methods described herein are potentially useful for improving growth conditions resulting in increased phosphorous uptake and/or yield for any type of plant. In one particular embodiment the plant is selected from the group consisting of non-legumes, legumes, *Brassica* spp., cereals, fruits, vegetables, nuts, flowers, and turf. Particularly the cereals are wheat, corn, rice, oat, rye, barley. Particularly legumes are lentil, chickpeas, beans, soybeans, peas, and alfalfa.

In another particular embodiment the plants are selected from the group consisting of alfalfa, rice, wheat, barley, rye, oat, cotton, sunflower, peanut, corn, potato, sweet potato, bean, pea, chickpeas, lentil, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

Seed Coatings

In another aspect, seeds are coated with one or more bacterial strains selected from the group consisting of:

the strain having the deposit accession number NRRL B-50608;

the strain having the deposit accession number NRRL B-50609;

the strain having the deposit accession number NRRL B-50610;

the strain having the deposit accession number NRRL B-50611;

the strain having the deposit accession number NRRL B-50612; or a mixture of two or more of the strains.

In a particular embodiment, the seed(s) is coated with one or more of the above mentioned deposited strains (e.g., including at least two of the above strains, at least three of the above strains, at least four of the above strains, up to and including all of the above strains).

In an embodiment, the seed(s) is coated with the strain having the deposit accession number NRRL B-50608. In an embodiment, the seed(s) is coated with the strain having the deposit accession number NRRL B-50609. In an embodiment, the seed(s) is coated with the strain having the deposit accession number NRRL B-50610. In an embodiment, the seed(s) is coated with the strain having the deposit accession number NRRL B-50611. In an embodiment, the seed(s) is coated with the strain having the deposit accession number NRRL B-50612.

In one embodiment, seeds may be treated with any of the composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed. Systems and apparati for performing these processes are commercially available from numerous suppliers, e.g., Bayer CropScience (Gustafson).

In another embodiment, the treatment entails coating seeds. One such process involves coating the inside wall of a round container with the composition(s) described herein, adding seeds, then rotating the container to cause the seeds to contact the wall and the composition(s), a process known in the art as "container coating". Seeds can be coated by combinations of coating methods. Soaking typically entails using liquid forms of the compositions described. For example, seeds can be soaked for about 1 minute to about 24 hours (e.g., for at least 1 min, 5 min, 10 min, 20 min, 40 min, 80 min, 3 hr, 6 hr, 12 hr, 24 hr).

In certain embodiments, a seed(s) coated with one or more of the compositions described herein will comprise $1\times10^1$-$1\times10^8$, more preferably $1\times10^2$-$1\times10^6$ colony forming units of one or more of the deposited bacterial strains per seed.

EXAMPLES

The following examples are provided for illustrative purposes and are not intended to limit the scope of the invention as claimed herein. Any variations in the exemplified examples which occur to the skilled artisan are intended to fall within the scope of the present invention.

Materials & Methods

Deposit of Biological Material

The following biological material has been deposited under the terms of the Budapest Treaty at the Microbial Genomics and Bioprocessing Research Unit (NRRL) National Center for Agricultural Utilization Research 1815 N. University Street, Peoria, Ill. 61604, USA and given the following accession number:

TABLE 1

Deposit of Biological Material

| Identification | Accession Number | Date of Deposit |
| --- | --- | --- |
| Bradyrhizobia japonicum | NRRL B-50612 | 30 Nov. 2011 |
| Bradyrhizobia japonicum | NRRL B-50611 | 30 Nov. 2011 |
| Bradyrhizobia japonicum | NRRL B-50610 | 30 Nov. 2011 |
| Bradyrhizobia japonicum | NRRL B-50609 | 30 Nov. 2011 |
| Bradyrhizobia japonicum | NRRL B-50608 | 30 Nov. 2011 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

Media

TABLE 2

Components of G16 medium.

| G16 Constituents (g/L Distilled deionized water (DDW)) | g/L |
|---|---|
| Potassium phosphate dibasic $K_2HPO_4$ | 0.550 |
| Magnesium sulphate heptahydrate $MgSO_4 \cdot 7H_2O$ | 0.200 |
| Calcium Chloride Dihydrate $CaCl_2 \cdot 2H_2O$ | 0.130 |
| Oxoid yeast extract (LP0021) | 0.750 |
| Ammonium chloride $NH_4Cl$ | 0.200 |
| L-Glutamic acid monosodium monohydrate | 0.250 |
| Sucrose | 1.500 |
| Dextrose Anhydrous | 4.500 |
| Iron (III) Chloride hexahydrate $FeCl_3 \cdot 6H_2O$ Stock (80 g/L DDW) stored at 4° C. for up to 6 months) | 0.200 |
| Corn steep solids (Sigma) | 0.400 |
| Trace Element Stock (see below)* | 365 μl |
| Vitamin Stock (see below) ** | 365 μl |
| pH | 6.800 |

TABLE 3

Trace element Stock Store at 4° C. for up to 6 months.

| Constituent (g/L DDW) | g/L |
|---|---|
| Nickel (II) Chloride Hexahydrate $NiCl_2 \cdot 6H_2O$ | 0.69 |
| Cupric sulfate pentahydrate $CuSO_4 \cdot 5H_2O$ | 0.22 |
| Boric Acid $H_3BO_3$ | 7.87 |
| Manganous sulfate monohydrate $MnSO_4 \cdot H_2O$ | 5.06 |
| Zinc sulfate heptahydrate $ZnSO_4 \cdot 7H_2O$ | 0.61 |
| Sodium molybdate $Na_2MoO_4 \cdot 2H_2O$ | 0.61 |
| Cobalt (II) hexahydrate $CoCl_2 \cdot 6H_2O$ | 0.66 |

*Trace elements are added with all other components before sterilization.

TABLE 4

Vitamin Stock - filter sterilized followed by storage at 4° C. for up to 6 months.

| Constituent (g/L DDW) | g/L |
|---|---|
| Thiamine Hydrochloride | 1.38 |
| Panthothenic acid | 0.55 |

**Vitamins are added after the media has been sterilized and has cooled, typically at time of inoculation.

TABLE 5

Components of Yeast Extract Mannitol (YEM) Medium.

| Yeast Extract Mannitol Agar (YEMA) Constituents (g/L DDW) | g/L or mL/L |
|---|---|
| Mannitol | 10.0 g |
| Oxoid Yeast Extract (LP0021) | 0.50 g |
| Sodium Chloride NaCl | 0.10 g |
| STOCK - Potassium phosphate dibasic $K_2HPO_4$ (50 g/1000 ml) | 10 mL |
| STOCK - Magnesium sulphate heptahydrate $MgSO_4 \cdot 7H_2O$ (20 g/1000 ml) | 10 mL |
| pH | 6.8 |

Example I

Determine 99.99% Kill Rate for USDA 532C

The following experiment(s), consisting of three (3) studies, was performed to determine the 99.99% kill rate for parental strain *Bradyrhizobia japonicum* USDA 532C.

Parental strain USDA 532C was grown in two 10 ml G16 (Tables 2-4) and YEM (Table 5) disposable culture tubes (VWR, 18×150 mm, #47729-583) for two days and harvested to obtain the highest cell concentration. This was achieved by combining both culture tubes into one tube and concentrating the cells down to 2 ml. Approximately fifty soybean seeds (variety Stine RR 1108-4) were surfaced sterilized in 50 ml sterile, disposable centrifuge tube (Fisher brand, #06-443-18) containing 5% household bleach solution for 30 seconds and rinsed with sterile deionized (DI) water. The sterilization step was repeated for five times. The seeds were immediately placed in a sterilized Petri dish and dried under the laminar hood. Once the seeds were completely dried and transferred to a 250 ml beaker, 1.5 ml of the concentrated parental strain USDA 532C culture was added to the seeds. The seeds were swirled in the beaker to evenly coat the seeds and allowed to dry under the hood. The beaker, containing the seeds, was wrapped with blue, sterilization paper and left in the hood until the experiment was completed. Time points were taken at zero time, every two days for one week, and every week until complete cell death occurred. Results are provided in Table 6.

TABLE 6

CFU per seed and percent kill rate for study 1.

| Number of days | CFU per seed | Percent kill rate |
|---|---|---|
| 0 | $3.06 \times 10^8$ | 0.00 |
| 3 | $3.72 \times 10^7$ | 87.86 |
| 7 | $4.20 \times 10^6$ | 98.63 |
| 14 | $3.07 \times 10^6$ | 99.00 |
| 18 | $6.43 \times 10^5$ | 99.79 |
| 24 | $2.87 \times 10^5$ | 99.91 |
| 37 | $2.64 \times 10^4$ | 99.99 |

As shown in Table 6 the initial CFU per seed for parental strain USDA 532C was $3.06 \times 10^8$ and at days 37 the CFU was at $2.64 \times 10^8$. The percent kill rate from times 0 to 37 days was calculated to be 99.99%.

The procedure was repeated except G16 was used as the initial growing medium. The results are provided in Table 7.

TABLE 7

CFU per seed and percent kill rate for study 2.

| Number of days | CFU per seed | Percent kill rate |
|---|---|---|
| 0 | $2.01 \times 10^9$ | 0.00 |
| 2 | $3.13 \times 10^8$ | 84.41 |
| 6 | $3.26 \times 10^7$ | 98.38 |
| 10 | $9.14 \times 10^6$ | 99.55 |
| 16 | $3.50 \times 10^6$ | 99.83 |
| 22 | $1.40 \times 10^6$ | 99.93 |
| 29 | $3.38 \times 10^5$ | 99.98 |
| 37 | $6.23 \times 10^4$ | 100.00 |

As shown in Table 7, when G16 was used as the initial growing medium it took from 29 to 37 days for the kill rate to reach 99.99%.

A third desiccation study was completed to determine if G16 and YEM media affected the rate of desiccation of parental strain USDA 532C. The results are provided in Tables 8 and 9 respectively.

TABLE 8

CFU per seed and percent kill rate for parental
strain USDA 532C grown G16 medium.

| Number of days | CFU per seed | Percent kill rate |
|---|---|---|
| 0 | $2.95 \times 10^9$ | 0.00 |
| 2 | $8.69 \times 10^7$ | 97.06 |
| 7 | $2.93 \times 10^7$ | 99.01 |
| 14 | $1.68 \times 10^7$ | 99.43 |
| 21 | $2.11 \times 10^6$ | 99.93 |
| 28 | $7.50 \times 10^4$ | 100.00 |

TABLE 9

CFU per seed and percent kill rate for parental
strain USDA 532C grown YEM medium.

| Number of days | CFU per seed | Percent kill rate |
|---|---|---|
| 0 | $2.90 \times 10^8$ | 0.00 |
| 2 | $3.46 \times 10^6$ | 98.81 |
| 7 | $1.81 \times 10^6$ | 99.38 |
| 14 | $1.31 \times 10^6$ | 99.55 |
| 21 | $7.33 \times 10^5$ | 99.75 |
| 28 | $7.00 \times 10^4$ | 99.98 |

As shown in Tables 8 and 9, there was no difference in the desiccation rate for parental strain USDA 532C when grown in G16 or YEM. The 99.99% kill rate was observed for the third study at approximately 28 days which is similar to what was observed in studies one (1) and two (2) supra.

Example II

Determine the Kill Rate of USDA 532C Using Ethyl Methanesulfonate (EMS)

The following experiment(s) were performed to determine the application rate of the mutagen, ethyl methanosulfonate (EMS) that would give a 99.9-99.99 percent kill rate for parental strain USDA 532C. This rate determination will become part of the mutagenesis protocol used to generate desiccation-resistant putative mutants although the method of mutagenesis may evolve for efficiency.

Inocula Preparation:

Parental strain USDA 532C was grown in six 10 ml YEM disposable culture tubes for two days and 5 ml of the culture was inoculated into four 250 ml flasks containing 50 ml YEM medium. The flasks were incubated for two days at 30° C. shaker. The culture from the flasks were subsequently centrifuged in 50 ml disposable sterile tubes at 8,000 rpm for ten minutes in a Sorvall RC 6 Plus® centrifuge and combined into one tube. The pellet was re-suspended in 4 ml of fresh YEM medium and separated into four 1.5 ml microcentrifuge tubes. The tubes would each represent different application rates used for the mutagenesis process.

Mutagenesis Process:

Once the culture have been aliquoted into separate tubes and the mutagen EMS (Sigma, C3H8O3S, FW 124.16, #M0880-1G) added to each tube, the tubes were vortexed vigorously and placed in an empty 250 ml flask. The flask containing the reaction tubes were incubated for 30 minutes at 30° C. in a shaker. Immediately following the incubation period, the tubes were washed five times with 0.16M sodium thiosulfate (STS, Fisher Chemical, Na2S2O3*5H2O, FW 248.18, #S445-3)) solution to inactivate the mutagen. After washing, the cells in the reaction tubes were sheared with 21 gauge syringe needle (BD 1 ml 21G1 Latex Free Syringe PrecisionGlide® Needle, 0.8 mm×25 mm, #309624) and dilutions were completed and plated on YEMA plates. The cell counts were available after five days incubation at 30° C. and the percent kill of the EMS application rate was calculated. To calculate the percent kill rate for each application rate, the following equation was used: ([cell count 0 µl EMS (control)−(cell count of µl EMS (treatment))÷cell count 0 µl EMS (control)]×100%). All other experiments following this experiment used this equation to calculate the percent kill rate. Results are provided in Table 10.

TABLE 10

Initial rates of EMS to determine upper limit
of mutagenesis for parental strain USDA 532C

| Application Rate | Cell counts (approximate cfu/ml) |
|---|---|
| 0 µl EMS (control) | $10^8$ cfu/ml |
| 1 µl EMS | similar results to 0 µl EMS $10^7$ cfu/ml |
| 10 µl EMS | similar results to 1 µl EMS |
| 100 µl EMS | 100% kill rate |

As shown in Table 10, the initial rates of EMS used were 0 µl, 1 µl, 10 µl and 100 µl. There was no difference among 0 µl, 1 µl, and 10 µl EMS, but 100 µl EMS resulted in 100% kill.

Experiments were repeated and refined to determine the acceptable kill rate. See Tables 11-17.

TABLE 11

Refining the rates of EMS to determine 99.9%
kill rate for parental strain USDA 532C

| Application Rate | Cell counts (approximate cfu/ml) | Percent kill rate |
|---|---|---|
| 0 µl EMS (control) | $2.49 \times 10^9$ cfu/ml | |
| 15 µl EMS | $2.24 \times 10^9$ cfu/ml | 10.17% |
| 25 µl EMS | $1.72 \times 10^9$ cfu/ml | 30.92% |
| 50 µl EMS | $1.67 \times 10^1$ cfu/ml | 100% |

From the initial finding, the amount of EMS used was narrowed to 0 µl, 15 µl, 25 µl and 50 µl EMS. As shown in Table 11, the percent kill rate was 10.17% to 30.92% for 15 µl and 25 µl EMS applications and 100% for 50 µl.

TABLE 12

Additional refinement of the application rates
of EMS for parental strain USDA 532C

| Application Rate | Cell counts (approximate cfu/ml) | Percent kill rate |
|---|---|---|
| 0 µl EMS (control) | $4.70 \times 10^9$ cfu/ml | |
| 25 µl EMS | $1.27 \times 10^9$ cfu/ml | 73.09% |
| 35 µl EMS | $5.37 \times 10^8$ cfu/ml | 88.58% |
| 50 µl EMS | $2.93 \times 10^2$ cfu/ml | 100% |

It was determined from Table 11 that 25 µl EMS was still too low of a kill rate. The application amounts for Table 12 were 0 µl, 25 µl, 35 µl, and 50 µl EMS. The application at 25 µl EMS had a higher kill rate than the results in Table 11 due to the decreased washing; therefore, the kill rate was higher than expected. However, the kill rate was still too low at 88.58% kill even when 35 µl EMS was used. See Table 12.

TABLE 13

Additional refinement of the application rates
of EMS for parental strain USDA 532C

| Application Rate | Cell counts (approximate cfu/ml) | Percent kill rate |
|---|---|---|
| 0 μl EMS (control) | $3.93 \times 10^9$ cfu/ml | |
| 40 μl EMS | $6.97 \times 10^8$ cfu/ml | 82.26% |
| 45 μl EMS | $8.57 \times 10^7$ cfu/ml | 97.82% |
| 50 μl EMS | $2.65 \times 10^5$ cfu/ml | 99.99% |

The amount of EMS used was increased to 40 μl, 45 μl, and 50 μl EMS. The EMS dose rates resulted in percent kill ranges of 82.26%-99.99%. See Table 13.

TABLE 14

Repeat application rate used in Table 13.

| Application Rate | Cell counts (approximate cfu/ml) | Percent kill rate |
|---|---|---|
| 0 μl EMS (control) | $7.07 \times 10^{11}$ cfu/ml | |
| 40 μl EMS | $1.35 \times 10^9$ cfu/ml | 99.81% |
| 45 μl EMS | $5.27 \times 10^8$ cfu/ml | 99.93% |
| 50 μl EMS | $2.19 \times 10^6$ cfu/ml | 100% |

The results provided in Table 13 were repeated again in Table 14 using the same EMS rates and this time the percent kill was 99.81% for 40 μl EMS and 99.93% for 45 μl EMS and 100% for 50 μl EMS. The desired kill rate of 99.9% was observed when 45 μl EMS was used so the application will be repeated. See Table 15.

TABLE 15

Repeat application rate used in Table 14.

| Application Rate | Cell counts (approximate cfu/ml) | Percent kill rate |
|---|---|---|
| 0 μl EMS (control) | $1.51 \times 10^8$ cfu/ml | |
| 45 μl EMS | $3.33 \times 10^4$ cfu/ml | 99.98% |
| 50 μl EMS | $4.33 \times 10^1$ cfu/ml | 100% |

The application rate of 45 μl EMS was duplicated to determine if the results in Table 14 were repeatable. The kill rate for 45 μl EMS was 99.98%. See Table 15.

Example III

Mutagenesis

The following experiment(s) were performed to generate putative desiccation-resistant mutants of strains parental strain USDA 532C using classical, e.g., chemical, mutagenesis.

Inocula Preparation:

A cell suspension of parental strain USDA 532C was made by taking a loop of cells from a fresh plate of USDA 532C by using a 10 ul sterile plastic loop (Fisher brand, #22-363-600) and mixing the cells in 1 ml sterilized, deionized (DI) water in 1.5 ml disposable microcentrifuge tube. The cell suspension was inoculated into two 250 ml flasks containing 50 ml YEM medium to achieve a final optical density (OD) $OD_{600nm}$ of 0.01. The flasks were incubated at 30° C. for three days and the cultures of the two flasks were combined. The culture was centrifuged for twenty minutes at 8,000 rpm in a Sorvall RC 6 Plus centrifuge. The supernatant was discarded and the pellet from re-suspended in 30 ml DI water. OD was taken of the concentrated culture and was inoculated into ten 250 ml flasks containing 50 ml YEM medium at OD=0.05. These flasks were incubated at 30° C. shaker for two days prior to the culture being used for mutagenesis.

Mutagenesis Process:

The cultures from the ten flasks were combined into a 1 L centrifuge bottle. Optical density of the combined cultures was recorded and the cultures were centrifuged for 20 minutes at 8,000 rpm in the Sorvall RC 6 Plus® centrifuge. The majority of the supernatant was discarded leaving approximately 30 ml of the supernatant in the centrifuge bottle. The supernatant was mixed with the pellet and transferred into a 50 ml sterile disposable centrifuge tube. The OD of the concentrated culture was taken and recorded. 1 ml of the concentrated culture was placed into six 1.5 ml disposable microcentrifuge tubes. The microcentrifuge tubes were centrifuged and the supernatant was discarded. This was repeated three more times or until the size of the pellet had reach the 0.1 ml mark on the microcentrifuge tube. The cells were mixed well with 1 ml fresh YEM medium using a sterile 1 ml 21 gauge syringe needle prior to the addition of the mutagen, ethyl methanesulfonate (EMS). The rates of mutagen added to each tube contained a high and a low dose with medium dosages between the high and low doses as indicated in Experiment II.

Immediately after the addition of EMS, the reaction tubes were placed in an empty 250 ml flask and incubated at 30° C. for 30 minutes. After incubation, the reaction tubes were centrifuged for one minute at 13,200 rpm using the Eppendorf Centrifuge 5415D. The supernatant of the reaction tubes was discarded. The mutagen in the reaction tubes was inactivated by washing five times with 1 ml of 0.16M sodium thiosulfate (STS) and mixed vigorously by vortexing the tubes. For each wash cycle, the reaction tubes were centrifuged after vortexing and the supernatant was discarded. After the fifth time, the reaction tubes were all combined into one 15 ml disposable tube for use in the enrichment process.

Example IV

Enrichment and Desiccation

The following experiment(s) were performed to enrich and desiccate the mutated cells of parental strain USDA 532C to eliminate wild type escapes and increase the putative mutant population and make it easier to isolate the mutant(s) that have desiccation-resistant characteristics.

Parental strain USDA 532C was subjected to the mutagenesis process mentioned in Example III. The mutated population of parental strain USDA 532C was enriched by inoculating 0.5 ml of the reaction into two 50 ml YEM flasks and incubating the cells for two days at 30° C. shaker. After two days, the cultures were desiccated by coating the cells onto soybean seeds and membrane filters and subjected to drying conditions. The culture from the enrichment step was adjusted to $OD_{600nm}$ of 0.5 before it was used to coat both soybean seeds and membrane filters.

Coating of Soybean Seeds:

Forty sterilized soybean seeds were coated with 0.5 ml of the culture. The seeds were placed in a 100 ml sterile beaker to dry under the laminar hood and covered with autoclave paper. Triplicate samples of the seeds were taken to get an initial CFU of the seeds. For each sample, three seeds were placed in a 15 ml disposable tube containing 5 ml sterile DI water and allowed to expand in the tube for approximately two hours before the suspension was serially diluted and spread onto YEMA plates. The remaining seeds left in the covered, beaker was placed under the hood for four days before the seeds were enriched.

To enrich the seeds, twenty seeds were placed into a 250 ml flask containing fresh 50 ml YEM. A final CFU was also taken when the seeds were enriched to determine the percent kill rate for the cell population. The same sampling was completed for the second time point as the initial time point. After the culture containing the seeds was incubated for two days, the culture was harvested by removing any seed debris by allowing the debris to settle before removing the supernatant. The supernatant of the culture was centrifuged and the pellet washed with sterile DI water prior to the culture being used to coat new sets of soybean seeds. This process was repeated until the calculated percent kill rate of the cell culture was less than 80%. Once 80% was achieved, the cell population was ready for isolation of the putative mutants for confirmation experiment.

Coating of Membrane Filters:

To control for soybean seed inconsistency and contamination issues, membrane filters were used as an alternative medium for cell coating. For membrane filters, 1 ml of the culture was used to coat both durapore (Millipore, 0.22 µm, PVDF, #GVWP02500) and isopore (Millipore, 0.4 µm, polycarbonate, #HTTP02500) membrane filters. For each type of filter, fifteen filters were coated by using a 25 mm Easy Pressure Syringe Filter Holder (VWR, #28144-109) and the filters were placed in sterile Petri dish containing two pieces of sterile, qualitative 125 mm Whatman paper (Whatman, #1001125). Once the filters were dried under the laminar hood, triplicates initial CFU were taken for each type of filter by placing one filter into a 15 ml disposable tube containing 5 ml sterile DI water and mixed by vortexing. After two hours soaking in the 15 ml tube, the filter suspension was diluted and plated onto YEMA plates. After the filters have dried under the hood for three days, eight filters were added into 250 ml flask with 50 ml fresh YEM and incubated at 30° C. for three days.

A final CFU was taken at the same time the filters were enriched to get the percent kill rate calculation. The same method was used for the final CFU as the initial CFU. The process of coating and drying was repeated until the percent kill rate was less than 80%. After 80% was achieved, single colony isolates were selected for further confirmation.

Example V

Confirmation of Putative Mutants

The following experiment(s) were to confirm the putative desiccation-resistant mutants by comparing their on-seed survivability after seed application with the original parent strain *Bradyrhizobium japonicum* strain USDA 532C.

Figure 2:
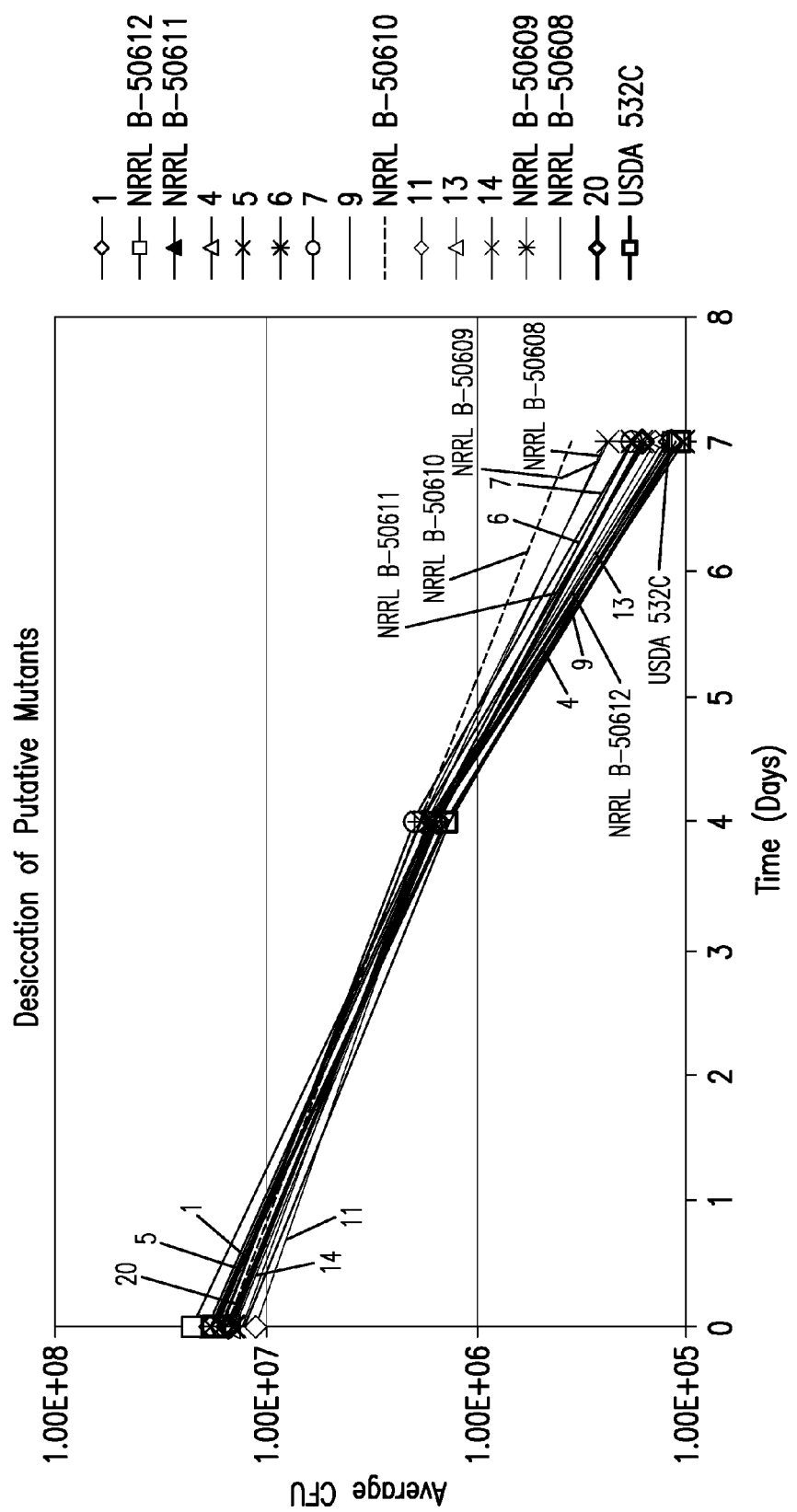
FIG. 2 is a graphical representation of the second screening of desiccation resistant mutants compared when compared to the desiccation resistance of parental strain USDA 532C.
Figure 3:
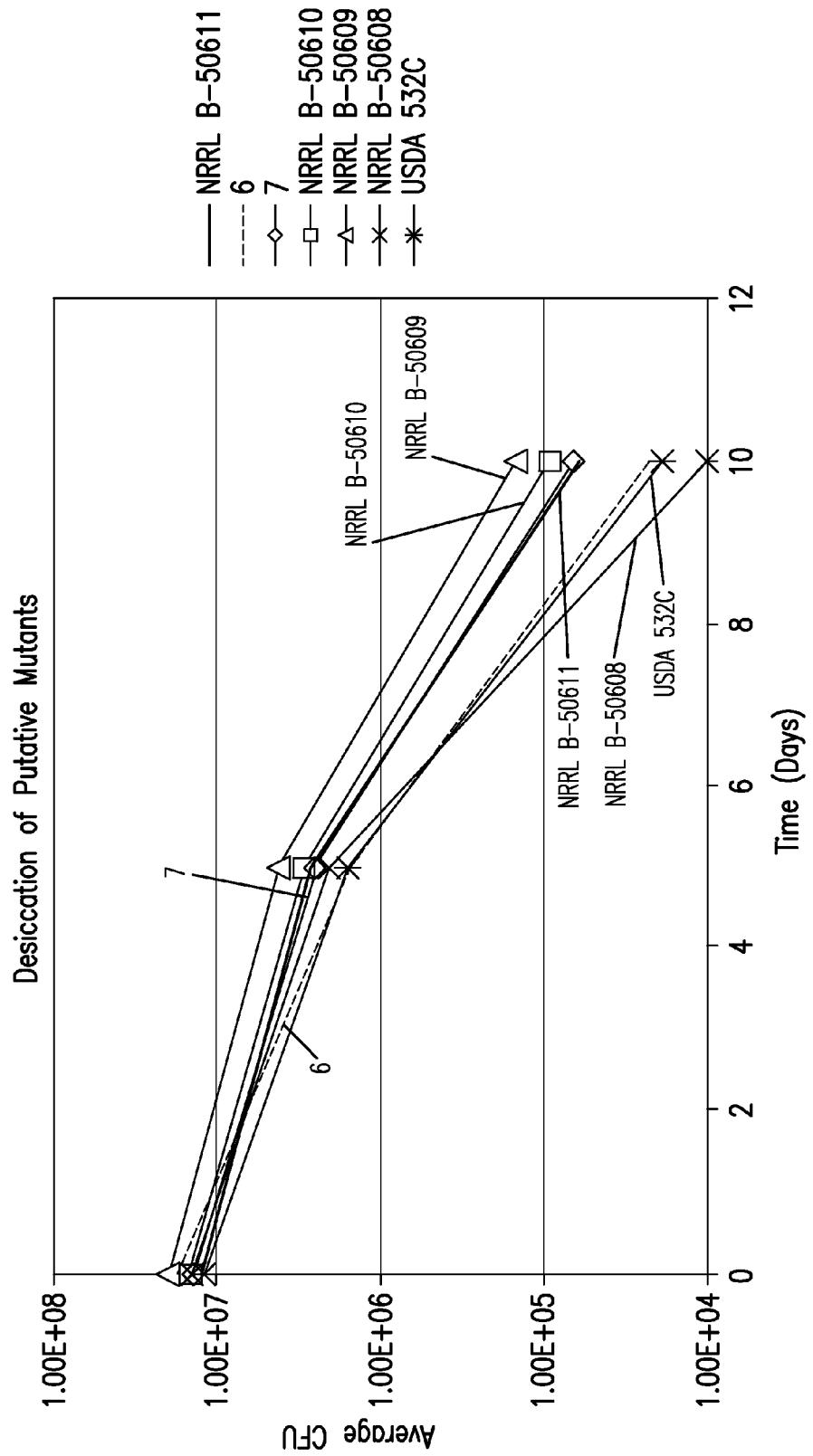
FIG. 3 is a graphical representation of the third screening of desiccation resistant mutants compared when compared to the desiccation resistance of parental strain USDA 532C.
Figure 4:
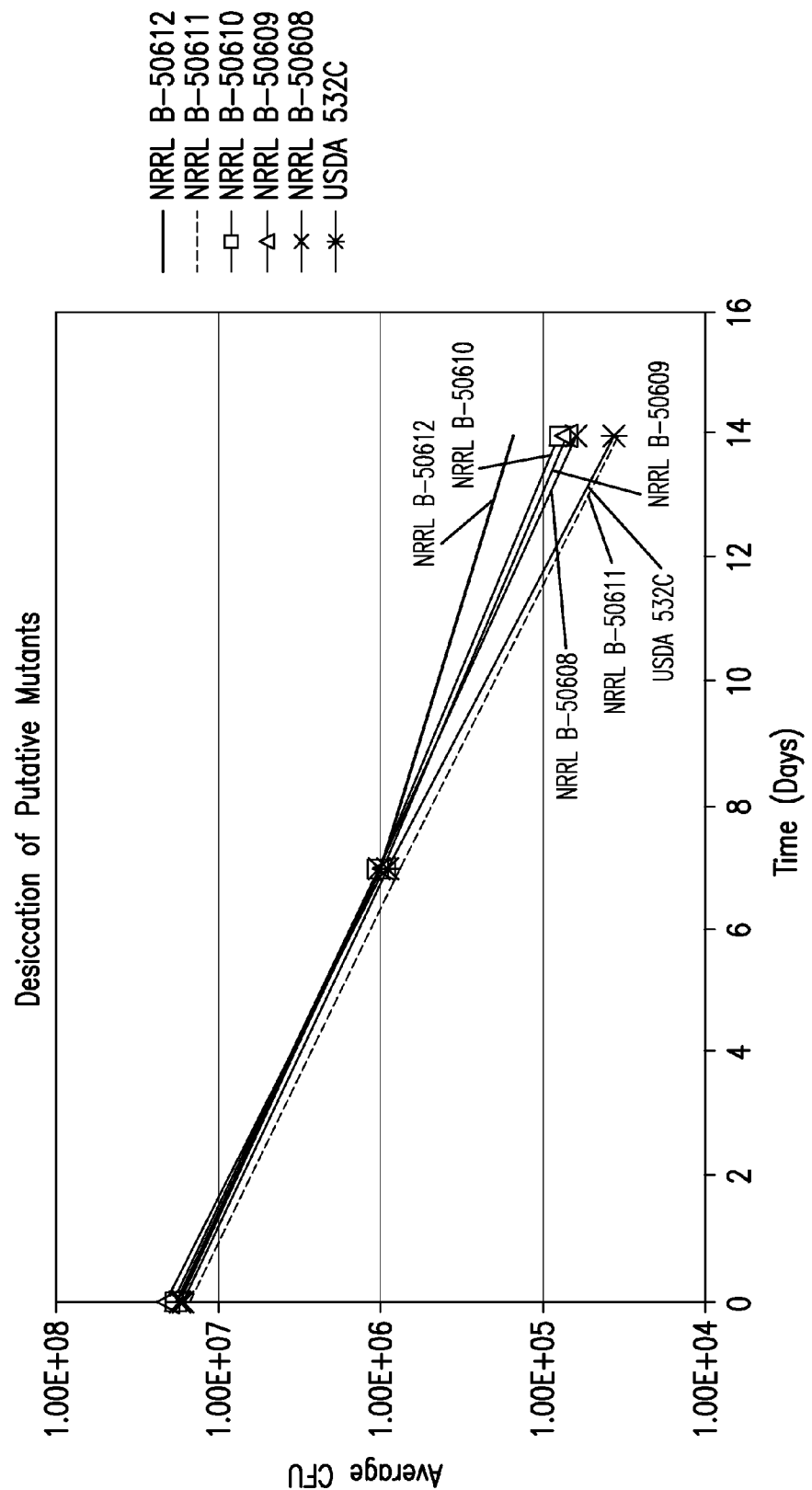
FIG. 4 is a graphical representation of the fourth screening of desiccation resistant mutants compared when compared to the desiccation resistance of parental strain USDA 532C.
Figure 5:
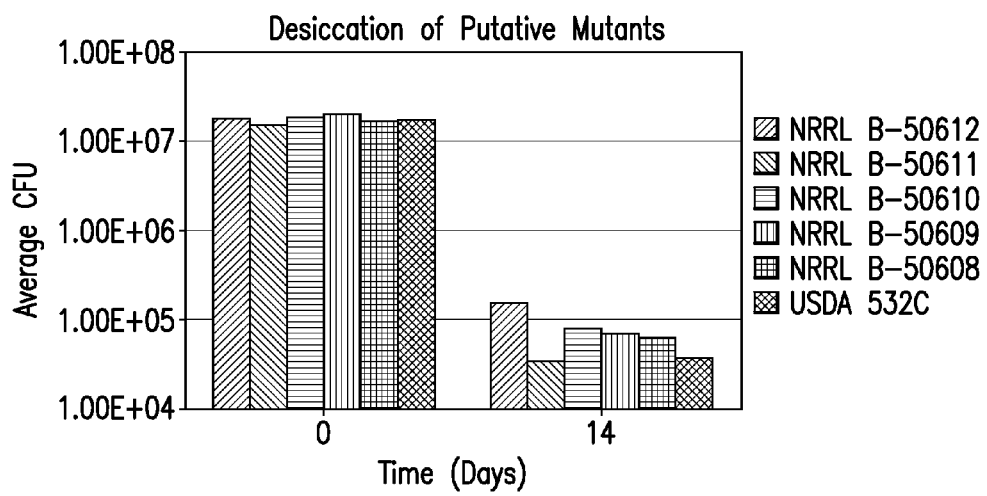
FIG. 5 is a bar graph representation of the desiccation resistance of the selected desiccation resistant mutants compared when compared to the desiccation resistance of parental strain USDA 532C at zero (0) and fourteen (14) days.
Figure 6:
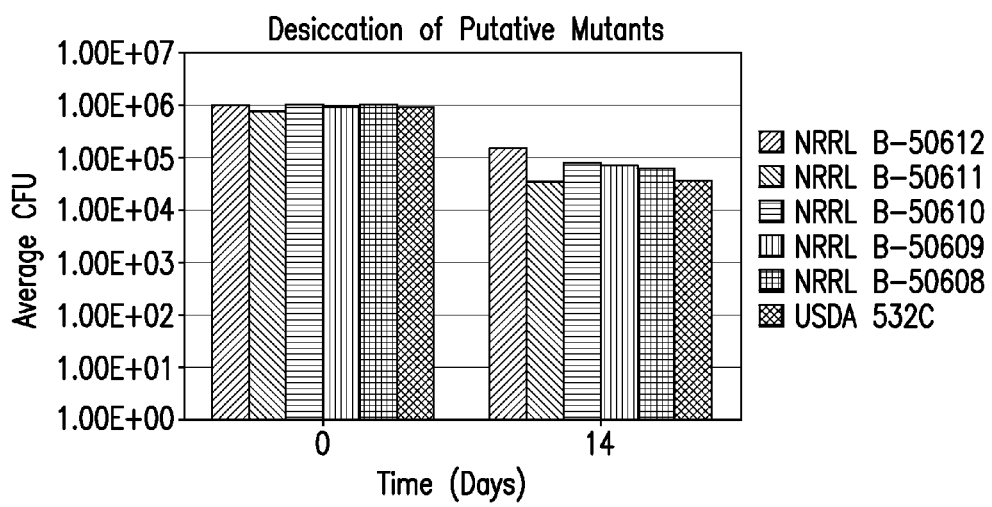
FIG. 6 is a bar graph representation of the desiccation resistance of the selected desiccation resistant mutants compared when compared to the desiccation resistance of parental strain USDA 532C at seven (7) and fourteen (14) days.

When 80% kill rate was observed for the seeds or filters, single colonies were randomly picked from the final time point and the putative mutants of a set of mutagenesis were analyzed for desiccation tolerance characteristic. The twenty single colonies picked from each set of mutagenesis results were individually grown in 250 ml flask containing 50 ml YEM medium. Each putative mutant strain was incubated at 30° C. shaker for three days and OD for each strain was adjusted to 0.5. Each strain was used to coat thirty unsterile soybean seeds with 0.5 ml culture in a 100 ml beaker covered by autoclave paper. Time points were taken at T=0, T=3, and T=7 days for the first round. Triplicate seed samplings were taken for each time point where each sample consisted of three seeds placed in 5 ml sterile DI water in 15 ml disposable tube. The seeds were allowed to expand for two hours before each sample was diluted and plated onto YEMA plates. After comparing the amount of cells recovered from each time point in relation to parental strain USDA 532C, any strain that performed better than the parent strain was subjected to a second round of confirmation. See FIG. 1. For the second round, the strains that had the best desiccation tolerance compared to the wild type were tested for desiccation again. See FIG. 2. Time points were taken at T=0, T=7, and T=14 days. The set of putative mutants from the second round was further confirmed for desiccation tolerance two more times. See FIGS. 3-6.

Twenty putative mutants of parental strain USDA 532C were isolated and screened for desiccation resistance. See FIGS. 1-3. Of the twenty putative strains tested, five putative mutant strains were confirmed for their desiccation tolerance characteristics when compared to the desiccation tolerance of parental strain, *Bradyrhizobium japonicum* strain USDA 532C. See FIGS. 4-6.

Example VI

Greenhouse Testing of Confirmed Mutant Strains

The following experiment(s) were performed to test the putative mutant strains in the greenhouse to test the performance of the mutant strains against the performance of the parent strain, USDA 532C.

The mutant strains having the best desiccation tolerance compared to the parent strain USDA 532C were tested in the greenhouse for performance against parental strain USDA 532C. The mutant and parent strains were grown in 50 ml YEM for two days before seed coating. Each strain was planted three different times; T=0, T=7, and T=14 days after seed coating. All time points were set up at the same time but the seeds were planted at the specified times. To set up for the time points, thirty soybean seeds were coated with 0.5 ml of culture at $OD_{600nm}$=0.5 in 100 ml beaker and the T=0 day time point was allowed to sit under the hood for 30 minutes before planting. The other two time points were allowed to dry completely and covered with autoclave paper. The seeds from the last two time points were planted at a later date. At each time point, two seeds were planted per pot for ten pots per strain. The leftover seeds were used to take a CFU for comparison with T=0. After nine weeks of growing in the greenhouse, the soybean pods were harvested from each plant from each time point and the dry weights were analyzed for statistical significance.

When the soybean pod weights of the mutant strains were compared to the parent strain at any of time points, there was no statistical significance at 95% confidence. This indicates that there was no performance difference between the mutant strains and parent strain that would affect the production of soybean pods when the mutant strains were used to coat soybean seeds.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A biologically pure culture of a mutagenized *Bradyrhizobium japonicum* strain selected from the group consisting of:
   the strain having the deposit accession number NRRL B-50612;
   the strain having the deposit accession number NRRL B-50611;
   the strain having the deposit accession number NRRL B-50610;
   the strain having the deposit accession number NRRL B-50609;
   and the strain having the deposit accession number NRRL B-50608.

2. A composition comprising one or more mutagenized *Bradyrhizobium japonicum* strain(s) according to claim 1 and an agriculturally suitable carrier.

3. The composition of claim 2, wherein the composition includes at least one agriculturally beneficial ingredient.

4. The composition of claim 3, wherein said at least one agriculturally beneficial ingredient includes one or more plant signal molecules.

5. The composition of claim 4, wherein said one or more plant signal molecules includes a lipo-chitooligosaccharide (LCO).

6. The composition of claim 5, wherein the LCO is synthetic.

7. The composition of claim 5, wherein the LCO is recombinant.

8. The composition of claim 5, wherein the LCO is naturally occurring.

9. The composition of claim 4, wherein said one or more plant signal molecules includes a chitinous compound.

10. The composition of claim 9, wherein the chitinous compound is a chito-oligomer (CO).

11. The composition of claim 10, wherein the CO is synthetic.

12. The composition of claim 10, wherein the CO is recombinant.

13. The composition of claim 10, wherein the CO is naturally occurring.

14. The composition of claim 4, wherein said one or more plant signal molecules includes a flavonoid.

15. A seed coated with a composition comprising one or more mutagenized *Bradyrhizobium japonicum* strain(s) according to claim 1.

16. The composition of claim 15, wherein the composition includes at least one agriculturally beneficial ingredient.

17. The composition of claim 16, wherein said at least one agriculturally beneficial ingredient includes one or more plant signal molecules.

* * * * *